US006603063B1

(12) United States Patent
Feitelson et al.

(10) Patent No.: US 6,603,063 B1
(45) Date of Patent: Aug. 5, 2003

(54) **PLANTS AND CELLS TRANSFORMED WITH A NUCLEIC ACID FROM *BACILLUS THURINGIENSIS* STRAIN KB59A4-6 ENCODING A NOVEL SUP TOXIN**

(75) Inventors: Jerald S. Feitelson, San Diego, CA (US); H. Ernest Schnepf, San Diego, CA (US); Kenneth E. Narva, San Diego, CA (US); Brian A. Stockhoff, San Diego, CA (US); James Schmeits, San Diego, CA (US); David Loewer, San Diego, CA (US); Charles Joseph Dullum, San Diego, CA (US); Judy Muller-Cohn, Del Mar, CA (US); Lisa Stamp, Solana Beach, CA (US); George Morrill, El Cajon, CA (US); Stacey Finstad-Lee, San Diego, CA (US)

(73) Assignee: Mycogen Corp., Indianapolis, IN (US)

( * ) Notice: Subject to any disclaimer, the term of this patent is extended or adjusted under 35 U.S.C. 154(b) by 0 days.

(21) Appl. No.: 09/307,106

(22) Filed: May 7, 1999

(51) Int. Cl.[7] .......................... A01H 5/00; C12N 1/21; C12N 5/04; C12N 15/32

(52) U.S. Cl. .................. 800/302; 536/23.71; 435/418; 435/252.3

(58) Field of Search ............................ 800/279, 302; 536/23.71; 435/418, 252.3

(56) References Cited

U.S. PATENT DOCUMENTS

| | | | |
|---|---|---|---|
| 4,448,885 | A | 5/1984 | Schnepf et al. |
| 4,467,036 | A | 8/1984 | Schnepf et al. |
| 4,797,276 | A | 1/1989 | Herrnstadt et al. |
| 4,853,331 | A | 8/1989 | Herrnstadt et al. |
| 4,918,006 | A | 4/1990 | Ellar et al. |
| 4,948,734 | A | 8/1990 | Edwards et al. |
| 4,990,332 | A | 2/1991 | Payne et al. |
| 5,039,523 | A | 8/1991 | Payne et al. |
| 5,093,120 | A | 3/1992 | Edwards et al. |
| 5,126,133 | A | 6/1992 | Payne et al. |
| 5,151,363 | A | 9/1992 | Payne |
| 5,164,180 | A | 11/1992 | Payne et al. |
| 5,169,629 | A | 12/1992 | Payne et al. |
| 5,236,843 | A | 8/1993 | Narva et al. |
| 5,262,399 | A | 11/1993 | Hickle et al. |
| 5,270,448 | A | 12/1993 | Payne |
| 5,281,530 | A | 1/1994 | Sick et al. |
| 5,322,932 | A | 6/1994 | Narva et al. |
| 5,426,049 | A | 6/1995 | Sick et al. |
| 5,439,881 | A | 8/1995 | Narva et al. |
| 5,667,993 | A | 9/1997 | Feitelson et al. |
| 5,670,365 | A | 9/1997 | Feitelson |

FOREIGN PATENT DOCUMENTS

| | | |
|---|---|---|
| EP | 0359472 | 3/1990 |
| WO | 9404684 | 3/1994 |
| WO | 9405771 | 3/1994 |
| WO | 9421795 | 9/1994 |

(List continued on next page.)

OTHER PUBLICATIONS

Lazar et al, 1988, Mol. Cell. Biol. 8:1247–1252.*

Hill et al, 1998, Biochem. Biophys. Res. Comm. 244:573–577.*

Gaertner, F. H., Leo Kim (1988) "Current Applied Recombinant DNA Projects" TIBTECH 6(4):54–57.

Gaertner, F. H. (1989) "Cellular Delivery Systems for Insecticidal Proteins: Living and Non–Living Microorganisms" in *Controlled Delivery of Crop Protection Agents*, R.M. Wilkins, ed., Taylor and Francis, New York and London, pp. 245–255.

Couch, T.L. (1980) "Mosquito Pthogenicity of *Bacillus thuringiensis* var. israelensis" in *Developments in Industrial Microbiology* 22:61–76.

Beegle, C.C. (1978) "Use of Entomogenous Bacteria in Agroccosystems" in *Developments in Industrial Microbiology* 20:97–104.

Krieg, V.A., et al. (1983) "*Bacillus thuringiensis* var. tenebrionis, a new pathotype effective against larvae of Coleoptera" Z. Ang. Ent. 96:500–508. Abstract.

Hofte, H., H.R. Whiteley (1989) "Insecticidal Cyrstal Proteins of *Bacillus thuringiensis*" Microbiological Reviews 53(2): 242–255.

Shevelev, A.B., et al. (1993) "Primary Structure of cryX**, the Novel δ–endotoxin–related gene from *Bacillus thuringiensis* spp. galleriae" FEBS 336(1): 79–82.

Smulevitch, S.V., et al. (1991) "Nucleotide Sequence of a Novel δ–Endotoxin Gene crylg of *Bacillus thuringiensis* ssp. galleriae" FEBS 293(1–2):25–28.

Schnepf, H.E., H.R. Whiteley (1981) "Cloning and Expression of the *Bacillus thuringiensis* Crystal Protein Gene in *Escheria coli*" Proc. Natl. Acad. Sci. USA 78(5): 2893–2897.

Estruch, J.J., et al. (1996) "Vip3A, A Novel *Bacillus thuringiensis* Vegetative Insecticidal Protein with a Wide Spectrum of Activities Against Lepidopteran Insects" Proc. Natl. Acad. Sci. USA 93:5389–5394.

Carozzi, N.B., et al. (1991) "Prediction of Insecticidal Activity of *Bacillus thuringiensis* Strains by Polymerase Chain Reaction Product Profiles" Applied and Environmental Microbiology 57(11):3057–3061.

Asano, Shoji, Hidetaka Hori, Yunlong Cui (1994) "A Unique Activity in *Bacillus thuringiensis* Growth Medium" Appl. Entomol. Zool. 29(1):39–45.

Li, Jade (1992) "Bacterial Toxins" Current Opinion in Structural Biology 2:545–556.

*Primary Examiner*—Amy Nelson
*Assistant Examiner*—Anne Kubelik
(74) *Attorney, Agent, or Firm*—Saliwanchik, Lloyd & Saliwanchik

(57) ABSTRACT

The specification discloses a nucleic acid from *Bacillus thuringiensis* strain KB59A4-6 that encodes a novel pesticidal SUP toxin and plants and microbial cells transformed with the nucleic acid.

12 Claims, No Drawings

FOREIGN PATENT DOCUMENTS

| | | |
|---|---|---|
| WO | 9424264 | 10/1994 |
| WO | 9605314 | 2/1996 |
| WO | 9610083 | 4/1996 |
| WO | 9818932 | 5/1998 |

* cited by examiner

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
(A) LENGTH: 2375 base pairs
(B) TYPE: nucleic acid
(C) STRANDEDNESS: single
(D) TOPOLOGY: linear -continued (ii) MOLECULE TYPE: DNA (genomic)

(vi) ORIGINAL SOURCE:
(C) INDIVIDUAL ISOLATE: Jav90

(xi) SEQUENCE DESCRIPTION: SEQ ID NO:1:

```
ATGAACAAGA ATAATACTAA ATTAAGCACA AGAGCCTTAC CAAGTTTTAT TGATTATTTT     60

AATGGCATTT ATGGATTTGC CACTGGTATC AAAGACATTA TGAACATGAT TTTTAAAACG    120

GATACAGGTG GTGATCTAAC CCTAGACGAA ATTTTAAAGA ATCAGCAGTT ACTAAATGAT    180

ATTTCTGGTA AATTGGATGG GGTGAATGGA AGCTTAAATG ATCTTATCGC ACAGGGAAAC    240

TTAAATACAG AATTATCTAA GGAAATATTA AAAATTGCAA ATGAACAAAA TCAAGTTTTA    300

AATGATGTTA ATAACAAACT CGATGCGATA AATACGATGC TTCGGGTATA TCTACCTAAA    360

ATTACCTCTA TGTTGAGTGA TGTAATGAAA CAAAATTATG CGCTAAGTCT GCAAATAGAA    420

TACTTAAGTA AACAATTGCA AGAGATTTCT GATAAGTTGG ATATTATTAA TGTAAATGTA    480

CTTATTAACT CTACACTTAC TGAAATTACA CCTGCGTATC AAAGGATTAA ATATGTGAAC    540

GAAAAATTTG AGGAATTAAC TTTTGCTACA GAAACTAGTT CAAAAGTAAA AAAGGATGGC    600

TCTCCTGCAG ATATTCTTGA TGAGTTAACT GAGTTAACTG AACTAGCGAA AAGTGTAACA    660

AAAAATGATG TGGATGGTTT TGAATTTTAC CTTAATACAT TCCACGATGT AATGGTAGGA    720

AATAATTTAT TCGGGCGTTC AGCTTTAAAA ACTGCATCGG AATTAATTAC TAAAGAAAAT    780

GTGAAAACAA GTGGCAGTGA GGTCGGAAAT GTTTATAACT TCTTAATTGT ATTAACAGCT    840

CTGCAAGCAA AAGCTTTTCT TACTTTAACA ACATGCCGAA AATTATTAGG CTTAGCAGAT    900

ATTGATTATA CTTCTATTAT GAATGAACAT TTAAATAAGG AAAAAGAGGA ATTTAGAGTA    960

AACATCCTCC CTACACTTTC TAATACTTTT TCTAATCCTA ATTATGCAAA AGTTAAAGGA   1020

AGTGATGAAG ATGCAAAGAT GATTGTGGAA GCTAAACCAG GACATGCATT GATTGGGTTT   1080

GAAATTAGTA ATGATTCAAT TACAGTATTA AAAGTATATG AGGCTAAGCT AAAACAAAAT   1140

TATCAAGTCG ATAAGGATTC CTTATCGGAA GTTATTTATG GTGATATGGA TAAATTATTG   1200

TGCCCAGATC AATCTGAACA AATCTATTAT ACAAATAACA TAGTATTTCC AAATGAATAT   1260

GTAATTACTA AAATTGATTT CACTAAAAAA ATGAAAACTT TAAGATATGA GGTAACAGCG   1320

AATTTTTATG ATTCTTCTAC AGGAGAAATT GACTTAAATA AGAAAAAAGT AGAATCAAGT   1380

GAAGCGGAGT ATAGAACGTT AAGTGCTAAT GATGATGGGG TGTATATGCC GTTAGGTGTC   1440

ATCAGTGAAA CATTTTTGAC TCCGATTAAT GGGTTTGGCC TCCAAGCTGA TGAAAATTCA   1500

AGATTAATTA CTTTAACATG TAAATCATAT TTAAGAGAAC TACTGCTAGC AACAGACTTA   1560

AGCAATAAAG AAACTAAATT GATYGTCCCG CCAAGTGGTT TTATTAGCAA TATTGTAGAG   1620

AACGGGTCCA TAGAAGAGGA CAATTTAGAG CCGTGGAAAG CAAATAATAA GAATGCGTAT   1680

GTAGATCATA CAGGCGGAGT GAATGGAACT AAAGCTTTAT ATGTTCATAA GGACGGAGGA   1740

ATTTCACAAT TTATTGGAGA TAAGTTAAAA CCGAAAACTG AGTATGTAAT CCAATATACT   1800

GTTAAAGGAA AACCTTCTAT TCATTTAAAA GATGAAAATA CTGGATATAT TCATTATGAA   1860

GATACAAATA ATAATTTAGA AGATTATCAA ACTATTAATA AACGTTTTAC TACAGGAACT   1920

GATTTAAAGG GAGTGTATTT AATTTTAAAA AGTCAAAATG GAGATGAAGC TTGGGGAGAT   1980

AACTTTATTA TTTTGGAAAT TAGTCCTTCT GAAAAGTTAT TAAGTCCAGA ATTAATTAAT   2040

ACAAATAATT GGACGAGTAC GGGATCAACT AATATTAGCG GTAATACACT CACTCTTTAT   2100

CAGGGAGGAC GAGGGATTCT AAAACAAAAC CTTCAATTAG ATAGTTTTTC AACTTATAGA   2160
```

-continued

```
GTGTATTTTT CTGTGTCCGG AGATGCTAAT GTAAGGATTA GAAATTCTAG GGAAGTGTTA   2220

TTTGAAAAAA GATATATGAG CGGTGCTAAA GATGTTTCTG AAATGTTCAC TACAAAATTT   2280

GAGAAAGATA ACTTTTATAT AGAGCTTTCT CAAGGGAATA ATTTATATGG TGGTCCTATT   2340

GTACATTTTT ACGATGTCTC TATTAAGTAA CCCAA                              2375
```

(2) INFORMATION FOR SEQ ID NO:2:

(i) SEQUENCE CHARACTERISTICS:
(A) LENGTH: 790 amino acids
(B) TYPE: amino acid
(C) STRANDEDNESS: single
(D) TOPOLOGY: linear (ii) MOLECULE TYPE: protein (vi) ORIGINAL SOURCE:
(C) INDIVIDUAL ISOLATE: Jav90

(xi) SEQUENCE DESCRIPTION: SEQ ID NO:2:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
```

-continued

```
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720
```

-continued

Val Tyr Phe Ser Val Ser Gly Asp Ala Asn Val Arg Ile Arg Asn Ser
725 730 735

Arg Glu Val Leu Phe Glu Lys Arg Tyr Met Ser Gly Ala Lys Asp Val
740 745 750

Ser Glu Met Phe Thr Thr Lys Phe Glu Lys Asp Asn Phe Tyr Ile Glu
755 760 765

Leu Ser Gln Gly Asn Asn Leu Tyr Gly Gly Pro Ile Val His Phe Tyr
770 775 780

Asp Val Ser Ile Lys Pro
785 790

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

GGRTTAMTTG GRTAYTATTT 20

(2) INFORMATION FOR SEQ ID NO:4:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

ATATCKWAYA TTKGCATTTA 20

(2) INFORMATION FOR SEQ ID NO:5:

(i) SEQUENCE CHARACTERISTICS:
(A) LENGTH: 1042 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 66D3

(xi) SEQUENCE DESCRIPTION: SEQ ID NO:5:

TTAATTGGGT ACTATTTTAA AGGAAAAGAT TTTAATAATC TTACTATATT TGCTCCAACA 60

CGTGAGAATA CTCTTATTTA TGATTTAGAA ACAGCGAATT CTTTATTAGA TAAGCAACAA 120

CAAACCTATC AATCTATTCG TTGGATCGGT TTAATAAAAA GCAAAAAAGC TGGAGATTTT 180

ACCTTTCAAT TATCGGATGA TGAGCATGCT ATTATAGAAA TCGATGGGAA AGTTATTTCG 240

CAAAAAGGCC AAAAGAAACA AGTTGTTCAT TTAGAAAAAG ATAAATTAGT TCCCATCAAA 300

ATTGAATATC AATCTGATAA AGCGTTAAAC CCAGATAGTC AAATGTTTAA AGAATTGAAA 360

TTATTTAAAA TAAATAGTCA AAAACAATCT CAGCAAGTGC AACAAGACGA ATTGAGAAAT 420

CCTGAATTTG GTAAAGAAAA AACTCAAACA TATTTAAAGA AAGCATCGAA AAGCAGCCTG 480

TTTAGCAATA AAAGTAAACG AGATATAGAT GAAGATATAG ATGAGGATAC AGATACAGAT 540

-continued

```
GGAGATGCCA TTCCTGATGT ATGGGAAGAA AATGGGTATA CCATCAAAGG AAGAGTAGCT    600

GTTAAATGGG ACGAAGGATT AGCTGATAAG GGATATAAAA AGTTTGTTTC CAATCCTTTT    660

AGACAGCACA CTGCTGGTGA CCCCTATAGT GACTATGAAA AGGCATCAAA AGATTTGGAT    720

TTATCTAATG CAAAAGAAAC ATTTAATCCA TTGGTGGCTG CTTTTCCAAG TGTCAATGTT    780

AGCTTGGAAA ATGTCACCAT ATCAAAAGAT GAAAATAAAA CTGCTGAAAT TGCGTCTACT    840

TCATCGAATA ATTGGTCCTA TACAAATACA GAGGGGGCAT CTATTGAAGC TGGAATTGGA    900

CCAGAAGGTT TGTTGTCTTT TGGAGTAAGT GCCAATTATC AACATTCTGA AACAGTGGCC    960

AAAGAGTGGG GTACAACTAA GGGAGACGCA ACACAATATA ATACAGCTTC AGCAGGATAT   1020

CTAAATGCCA ATGTACGATA TA                                            1042
```

(2) INFORMATION FOR SEQ ID NO:6:

(i) SEQUENCE CHARACTERISTICS:
(A) LENGTH: 347 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 66D3

(xi) SEQUENCE DESCRIPTION: SEQ ID NO:6:

```
Leu Ile Gly Tyr Tyr Phe Lys Gly Lys Asp Phe Asn Asn Leu Thr Ile
1               5                   10                  15

Phe Ala Pro Thr Arg Glu Asn Thr Leu Ile Tyr Asp Leu Glu Thr Ala
            20                  25                  30

Asn Ser Leu Leu Asp Lys Gln Gln Gln Thr Tyr Gln Ser Ile Arg Trp
        35                  40                  45

Ile Gly Leu Ile Lys Ser Lys Lys Ala Gly Asp Phe Thr Phe Gln Leu
    50                  55                  60

Ser Asp Asp Glu His Ala Ile Ile Glu Ile Asp Gly Lys Val Ile Ser
65                  70                  75                  80

Gln Lys Gly Gln Lys Lys Gln Val Val His Leu Glu Lys Asp Lys Leu
                85                  90                  95

Val Pro Ile Lys Ile Glu Tyr Gln Ser Asp Lys Ala Leu Asn Pro Asp
            100                 105                 110

Ser Gln Met Phe Lys Glu Leu Lys Leu Phe Lys Ile Asn Ser Gln Lys
        115                 120                 125

Gln Ser Gln Gln Val Gln Gln Asp Glu Leu Arg Asn Pro Glu Phe Gly
    130                 135                 140

Lys Glu Lys Thr Gln Thr Tyr Leu Lys Lys Ala Ser Lys Ser Ser Leu
145                 150                 155                 160

Phe Ser Asn Lys Ser Lys Arg Asp Ile Asp Glu Asp Ile Asp Glu Asp
                165                 170                 175

Thr Asp Thr Asp Gly Asp Ala Ile Pro Asp Val Trp Glu Glu Asn Gly
            180                 185                 190

Tyr Thr Ile Lys Gly Arg Val Ala Val Lys Trp Asp Glu Gly Leu Ala
        195                 200                 205

Asp Lys Gly Tyr Lys Lys Phe Val Ser Asn Pro Phe Arg Gln His Thr
    210                 215                 220

Ala Gly Asp Pro Tyr Ser Asp Tyr Glu Lys Ala Ser Lys Asp Leu Asp
225                 230                 235                 240
```

-continued

```
Leu Ser Asn Ala Lys Glu Thr Phe Asn Pro Leu Val Ala Ala Phe Pro
                245                 250                 255

Ser Val Asn Val Ser Leu Glu Asn Val Thr Ile Ser Lys Asp Glu Asn
            260                 265                 270

Lys Thr Ala Glu Ile Ala Ser Thr Ser Ser Asn Asn Trp Ser Tyr Thr
        275                 280                 285

Asn Thr Glu Gly Ala Ser Ile Glu Ala Gly Ile Gly Pro Glu Gly Leu
    290                 295                 300

Leu Ser Phe Gly Val Ser Ala Asn Tyr Gln His Ser Glu Thr Val Ala
305                 310                 315                 320

Lys Glu Trp Gly Thr Thr Lys Gly Asp Ala Thr Gln Tyr Asn Thr Ala
                325                 330                 335

Ser Ala Gly Tyr Leu Asn Ala Asn Val Arg Tyr
            340                 345
```

(2) INFORMATION FOR SEQ ID NO:7:

(i) SEQUENCE CHARACTERISTICS:
(A) LENGTH: 2645 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: PS177C8a (xi) SEQUENCE DESCRIPTION: SEQ ID NO:7:

```
ATGAAGAAGA AGTTAGCAAG TGTTGTAACG TGTACGTTAT TAGCTCCTAT GTTTTTGAAT     60

GGAAATGTGA ATGCTGTTTA CGCAGACAGC AAAACAAATC AAATTTCTAC AACACAGAAA    120

AATCAACAGA AAGAGATGGA CCGAAAAGGA TTACTTGGGT ATTATTTCAA AGGAAAAGAT    180

TTTAGTAATC TTACTATGTT TGCACCGACA CGTGATAGTA CTCTTATTTA TGATCAACAA    240

ACAGCAAATA AACTATTAGA TAAAAAACAA CAAGAATATC AGTCTATTCG TTGGATTGGT    300

TTGATTCAGA GTAAAGAAAC GGGAGATTTC ACATTTAACT TATCTGAGGA TGAACAGGCA    360

ATTATAGAAA TCAATGGGAA AATTATTTCT AATAAAGGGA AAGAAAAGCA AGTTGTCCAT    420

TTAGAAAAAG GAAAATTAGT TCCAATCAAA ATAGAGTATC AATCAGATAC AAAATTTAAT    480

ATTGACAGTA AAACATTTAA AGAACTTAAA TTATTTAAAA TAGATAGTCA AAACCAACCC    540

CAGCAAGTCC AGCAAGATGA ACTGAGAAAT CCTGAATTTA ACAAGAAAGA ATCACAGGAA    600

TTCTTAGCGA AACCATCGAA AATAAATCTT TTCACTCAAA AATGAAAAG GGAAATTGAT     660

GAAGACACGG ATACGGATGG GGACTCTATT CCTGACCTTT GGGAAGAAAA TGGGTATACG    720

ATTCAAAATA GAATCGCTGT AAAGTGGGAC GATTCTYTAG CAAGTAAAGG GTATACGAAA    780

TTTGTTTCAA ATCCGCTAGA AAGTCACACA GTTGGTGATC CTTATACAGA TTATGAAAAG    840

GCAGCAAGAG ACCTAGATTT GTCAAATGCA AAGGAAACGT TTAACCCATT GGTAGCTGCT    900

TTTCCAAGTG TGAATGTTAG TATGGAAAAG GTGATATTAT CACCAAATGA AAATTTATCC    960

AATAGTGTAG AGTCTCATTC ATCCACGAAT TGGTCTTATA CAAATACAGA AGGTGCTTCT   1020

GTTGAAGCGG GGATTGGACC AAAAGGTATT TCGTTCGGAG TTAGCGTAAA CTATCAACAC   1080

TCTGAAACAG TTGCACAAGA ATGGGGAACA TCTACAGGAA ATACTTCGCA ATTCAATACG   1140

GCTTCAGCGG GATATTTAAA TGCAAATGTT CGATATAACA ATGTAGGAAC TGGTGCCATC   1200

TACGATGTAA AACCTACAAC AAGTTTTGTA TTAAATAACG ATACTATCGC AACTATTACG   1260
```

-continued

```
GCGAAATCTA ATTCTACAGC CTTAAATATA TCTCCTGGAG AAAGTTACCC GAAAAAAGGA   1320

CAAAATGGAA TCGCAATAAC ATCAATGGAT GATTTTAATT CCCATCCGAT TACATTAAAT   1380

AAAAAACAAG TAGATAATCT GCTAAATAAT AAACCTATGA TGTTGGAAAC AAACCAAACA   1440

GATGGTGTTT ATAAGATAAA AGATACACAT GGAAATATAG TAACTGGCGG AGAATGGAAT   1500

GGTGTCATAC AACAAATCAA GGCTAAAACA GCGTCTATTA TTGTGGATGA TGGGGAACGT   1560

GTAGCAGAAA AACGTGTAGC GGCAAAAGAT TATGAAAATC CAGAAGATAA AACACCGTCT   1620

TTAACTTTAA AAGATGCCCT GAAGCTTTCA TATCCAGATG AAATAAAAGA AATAGAGGGA   1680

TTATTATATT ATAAAAACAA ACCGATATAC GAATCGAGCG TTATGACTTA CTTAGATGAA   1740

AATACAGCAA AAGAAGTGAC CAAACAATTA AATGATACCA CTGGGAAATT TAAAGATGTA   1800

AGTCATTTAT ATGATGTAAA ACTGACTCCA AAAATGAATG TTACAATCAA ATTGTCTATA   1860

CTTTATGATA ATGCTGAGTC TAATGATAAC TCAATTGGTA AATGGACAAA CACAAATATT   1920

GTTTCAGGTG GAAATAACGG AAAAAAACAA TATTCTTCTA ATAATCCGGA TGCTAATTTG   1980

ACATTAAATA CAGATGCTCA AGAAAAATTA AATAAAAATC GTACTATTAT ATAAGTTTAT   2040

ATATGAAGTC AGAAAAAAAC ACACAATGTG AGATTACTAT AGATGGGGAG ATTTATCCGA   2100

TCACTACAAA AACAGTGAAT GTGAATAAAG ACAATTACAA AAGATTAGAT ATTATAGCTC   2160

ATAATATAAA AAGTAATCCA ATTTCTTCAA TTCATATTAA AACGAATGAT GAAATAACTT   2220

TATTTTGGGA TGATATTTCT ATAACAGATG TAGCATCAAT AAAACCGGAA AATTTAACAG   2280

ATTCAGAAAT TAAACAGATT TATAGTAGGT ATGGTATTAA GTTAGAAGAT GGAATCCTTA   2340

TTGATAAAAA AGGTGGGATT CATTATGGTG AATTTATTAA TGAAGCTAGT TTTAATATTG   2400

AACCATTGCA AAATTATGTG ACAAAATATA AAGTTACTTA TAGTAGTGAG TTAGGACAAA   2460

ACGTGAGTGA CACACTTGAA AGTGATAAAA TTTACAAGGA TGGGACAATT AAATTTGATT   2520

TTACAAAATA TAGTRAAAAT GAACAAGGAT TATTTTATGA CAGTGGATTA AATTGGGACT   2580

TTAAAATTAA TGCTATTACT TATGATGGTA AAGAGATGAA TGTTTTTCAT AGATATAATA   2640

AATAG                                                               2645
```

(2) INFORMATION FOR SEQ ID NO:8:

(i) SEQUENCE CHARACTERISTICS:
(A) LENGTH: 881 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: PS177C8a (xi) SEQUENCE DESCRIPTION: SEQ ID NO:8:

```
Met Lys Lys Lys Leu Ala Ser Val Val Thr Cys Thr Leu Leu Ala Pro
1               5                   10                  15

Met Phe Leu Asn Gly Asn Val Asn Ala Val Tyr Ala Asp Ser Lys Thr
            20                  25                  30

Asn Gln Ile Ser Thr Thr Gln Lys Asn Gln Gln Lys Glu Met Asp Arg
        35                  40                  45

Lys Gly Leu Leu Gly Tyr Tyr Phe Lys Gly Lys Asp Phe Ser Asn Leu
    50                  55                  60

Thr Met Phe Ala Pro Thr Arg Asp Ser Thr Leu Ile Tyr Asp Gln Gln
65                  70                  75                  80
```

-continued

```
Thr Ala Asn Lys Leu Leu Asp Lys Lys Gln Gln Glu Tyr Gln Ser Ile
                85                  90                  95

Arg Trp Ile Gly Leu Ile Gln Ser Lys Glu Thr Gly Asp Phe Thr Phe
            100                 105                 110

Asn Leu Ser Glu Asp Glu Gln Ala Ile Ile Glu Ile Asn Gly Lys Ile
        115                 120                 125

Ile Ser Asn Lys Gly Lys Glu Lys Gln Val Val His Leu Glu Lys Gly
    130                 135                 140

Lys Leu Val Pro Ile Lys Ile Glu Tyr Gln Ser Asp Thr Lys Phe Asn
145                 150                 155                 160

Ile Asp Ser Lys Thr Phe Lys Glu Leu Lys Leu Phe Lys Ile Asp Ser
                165                 170                 175

Gln Asn Gln Pro Gln Gln Val Gln Gln Asp Glu Leu Arg Asn Pro Glu
            180                 185                 190

Phe Asn Lys Lys Glu Ser Gln Glu Phe Leu Ala Lys Pro Ser Lys Ile
        195                 200                 205

Asn Leu Phe Thr Gln Lys Met Lys Arg Glu Ile Asp Glu Asp Thr Asp
    210                 215                 220

Thr Asp Gly Asp Ser Ile Pro Asp Leu Trp Glu Glu Asn Gly Tyr Thr
225                 230                 235                 240

Ile Gln Asn Arg Ile Ala Val Lys Trp Asp Asp Ser Leu Ala Ser Lys
                245                 250                 255

Gly Tyr Thr Lys Phe Val Ser Asn Pro Leu Glu Ser His Thr Val Gly
            260                 265                 270

Asp Pro Tyr Thr Asp Tyr Glu Lys Ala Ala Arg Asp Leu Asp Leu Ser
        275                 280                 285

Asn Ala Lys Glu Thr Phe Asn Pro Leu Val Ala Ala Phe Pro Ser Val
    290                 295                 300

Asn Val Ser Met Glu Lys Val Ile Leu Ser Pro Asn Glu Asn Leu Ser
305                 310                 315                 320

Asn Ser Val Glu Ser His Ser Ser Thr Asn Trp Ser Tyr Thr Asn Thr
                325                 330                 335

Glu Gly Ala Ser Val Glu Ala Gly Ile Gly Pro Lys Gly Ile Ser Phe
            340                 345                 350

Gly Val Ser Val Asn Tyr Gln His Ser Glu Thr Val Ala Gln Glu Trp
        355                 360                 365

Gly Thr Ser Thr Gly Asn Thr Ser Gln Phe Asn Thr Ala Ser Ala Gly
    370                 375                 380

Tyr Leu Asn Ala Asn Val Arg Tyr Asn Asn Val Gly Thr Gly Ala Ile
385                 390                 395                 400

Tyr Asp Val Lys Pro Thr Thr Ser Phe Val Leu Asn Asn Asp Thr Ile
                405                 410                 415

Ala Thr Ile Thr Ala Lys Ser Asn Ser Thr Ala Leu Asn Ile Ser Pro
            420                 425                 430

Gly Glu Ser Tyr Pro Lys Lys Gly Gln Asn Gly Ile Ala Ile Thr Ser
        435                 440                 445

Met Asp Asp Phe Asn Ser His Pro Ile Thr Leu Asn Lys Lys Gln Val
    450                 455                 460

Asp Asn Leu Leu Asn Asn Lys Pro Met Met Leu Glu Thr Asn Gln Thr
465                 470                 475                 480

Asp Gly Val Tyr Lys Ile Lys Asp Thr His Gly Asn Ile Val Thr Gly
                485                 490                 495
```

-continued

```
Gly Glu Trp Asn Gly Val Ile Gln Gln Ile Lys Ala Lys Thr Ala Ser
            500                 505                 510

Ile Ile Val Asp Asp Gly Glu Arg Val Ala Glu Lys Arg Val Ala Ala
        515                 520                 525

Lys Asp Tyr Glu Asn Pro Glu Asp Lys Thr Pro Ser Leu Thr Leu Lys
    530                 535                 540

Asp Ala Leu Lys Leu Ser Tyr Pro Asp Glu Ile Lys Glu Ile Glu Gly
545                 550                 555                 560

Leu Leu Tyr Tyr Lys Asn Lys Pro Ile Tyr Glu Ser Ser Val Met Thr
                565                 570                 575

Tyr Leu Asp Glu Asn Thr Ala Lys Glu Val Thr Lys Gln Leu Asn Asp
            580                 585                 590

Thr Thr Gly Lys Phe Lys Asp Val Ser His Leu Tyr Asp Val Lys Leu
        595                 600                 605

Thr Pro Lys Met Asn Val Thr Ile Lys Leu Ser Ile Leu Tyr Asp Asn
    610                 615                 620

Ala Glu Ser Asn Asp Asn Ser Ile Gly Lys Trp Thr Asn Thr Asn Ile
625                 630                 635                 640

Val Ser Gly Gly Asn Asn Gly Lys Lys Gln Tyr Ser Ser Asn Asn Pro
                645                 650                 655

Asp Ala Asn Leu Thr Leu Asn Thr Asp Ala Gln Glu Lys Leu Asn Lys
            660                 665                 670

Asn Arg Asp Tyr Tyr Ile Ser Leu Tyr Met Lys Ser Glu Lys Asn Thr
        675                 680                 685

Gln Cys Glu Ile Thr Ile Asp Gly Glu Ile Tyr Pro Ile Thr Thr Lys
    690                 695                 700

Thr Val Asn Val Asn Lys Asp Asn Tyr Lys Arg Leu Asp Ile Ile Ala
705                 710                 715                 720

His Asn Ile Lys Ser Asn Pro Ile Ser Ser Ile His Ile Lys Thr Asn
                725                 730                 735

Asp Glu Ile Thr Leu Phe Trp Asp Asp Ile Ser Ile Thr Asp Val Ala
            740                 745                 750

Ser Ile Lys Pro Glu Asn Leu Thr Asp Ser Glu Ile Lys Gln Ile Tyr
        755                 760                 765

Ser Arg Tyr Gly Ile Lys Leu Glu Asp Gly Ile Leu Ile Asp Lys Lys
    770                 775                 780

Gly Gly Ile His Tyr Gly Glu Phe Ile Asn Glu Ala Ser Phe Asn Ile
785                 790                 795                 800

Glu Pro Leu Gln Asn Tyr Val Thr Lys Tyr Lys Val Thr Tyr Ser Ser
                805                 810                 815

Glu Leu Gly Gln Asn Val Ser Asp Thr Leu Glu Ser Asp Lys Ile Tyr
            820                 825                 830

Lys Asp Gly Thr Ile Lys Phe Asp Phe Thr Lys Tyr Ser Xaa Asn Glu
        835                 840                 845

Gln Gly Leu Phe Tyr Asp Ser Gly Leu Asn Trp Asp Phe Lys Ile Asn
    850                 855                 860

Ala Ile Thr Tyr Asp Gly Lys Glu Met Asn Val Phe His Arg Tyr Asn
865                 870                 875                 880

Lys
```

(2) INFORMATION FOR SEQ ID NO:9:

(i) SEQUENCE CHARACTERISTICS:
(A) LENGTH: 1022 base pairs

-continued (B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: 177I8

(xi) SEQUENCE DESCRIPTION: SEQ ID NO:9:

```
TGGATTAATT GGGTATTATT TCAAAGGAAA AGATTTTAAT AATCTTACTA TGTTTGCACC     60

GACACGTGAT AATACCCTTA TGTATGACCA ACAAACAGCG AATGCATTAT TAGATAAAAA    120

ACAACAAGAA TATCAGTCCA TTCGTTGGAT TGGTTTGATT CAGAGTAAAG AAACGGGCGA    180

TTTCACATTT AACTTATCAA AGGATGAACA GGCAATTATA GAAATCGATG GGAAAATCAT    240

TTCTAATAAA GGGAAAGAAA AGCAAGTTGT CCATTTAGAA AAAGAAAAAT TAGTTCCAAT    300

CAAAATAGAG TATCAATCAG ATACGAAATT TAATATTGAT AGTAAAACAT TTAAAGAACT    360

TAAATTATTT AAAATAGATA GTCAAAACCA ATCTCAACAA GTTCAACTGA GAAACCCTGA    420

ATTTAACAAA AAAGAATCAC AGGAATTTTT AGCAAAAGCA TCAAAAACAA ACCTTTTTAA    480

GCAAAAAATG AAAAGAGATA TTGATGAAGA TACGGATACA GATGGAGACT CCATTCCTGA    540

TCTTTGGGAA GAAAATGGGT ACACGATTCA AAATAAAGTT GCTGTCAAAT GGGATGATTC    600

GCTAGCAAGT AAGGGATATA CAAAATTTGT TTCGAATCCA TTAGACAGCC ACACAGTTGG    660

CGATCCCTAT ACTGATTATG AAAAGGCCGC AAGGGATTTA GATTTATCAA ATGCAAAGGA    720

AACGTTCAAC CCATTGGTAG CTGCTTTTCC AAGTGTGAAT GTTAGTATGG AAAAGGTGAT    780

ATTATCACCA AATGAAAATT TATCCAATAG TGTAGAGTCT CATTCATCCA CGAATTGGTC    840

TTATACGAAT ACAGAAGGAG CTTCCATTGA AGCTGGTGGC GGTCCATTAG GCCTTTCTTT    900

TGGAGTGAGT GTTAATTATC AACACTCTGA AACAGTTGCA CAAGAATGGG GAACATCTAC    960

AGGAAATACT TCACAATTCA ATACGGCTTC AGCGGGATAT TTAAATGCCA ATATACGATA   1020

TA                                                                  1022
```

(2) INFORMATION FOR SEQ ID NO:10:

(i) SEQUENCE CHARACTERISTICS:
(A) LENGTH: 340 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: 177I8

(xi) SEQUENCE DESCRIPTION: SEQ ID NO:10:

```
Gly Leu Ile Gly Tyr Tyr Phe Lys Gly Lys Asp Phe Asn Asn Leu Thr
1               5                   10                  15

Met Phe Ala Pro Thr Arg Asp Asn Thr Leu Met Tyr Asp Gln Gln Thr
            20                  25                  30

Ala Asn Ala Leu Leu Asp Lys Lys Gln Gln Glu Tyr Gln Ser Ile Arg
        35                  40                  45

Trp Ile Gly Leu Ile Gln Ser Lys Glu Thr Gly Asp Phe Thr Phe Asn
    50                  55                  60

Leu Ser Lys Asp Glu Gln Ala Ile Ile Glu Ile Asp Gly Lys Ile Ile
65                  70                  75                  80

Ser Asn Lys Gly Lys Glu Lys Gln Val Val His Leu Glu Lys Glu Lys
```

-continued

```
                85                  90                  95

Leu Val Pro Ile Lys Ile Glu Tyr Gln Ser Asp Thr Lys Phe Asn Ile
            100                 105                 110

Asp Ser Lys Thr Phe Lys Glu Leu Lys Leu Phe Lys Ile Asp Ser Gln
        115                 120                 125

Asn Gln Ser Gln Gln Val Gln Leu Arg Asn Pro Glu Phe Asn Lys Lys
    130                 135                 140

Glu Ser Gln Glu Phe Leu Ala Lys Ala Ser Lys Thr Asn Leu Phe Lys
145                 150                 155                 160

Gln Lys Met Lys Arg Asp Ile Asp Glu Asp Thr Asp Thr Asp Gly Asp
                165                 170                 175

Ser Ile Pro Asp Leu Trp Glu Glu Asn Gly Tyr Thr Ile Gln Asn Lys
            180                 185                 190

Val Ala Val Lys Trp Asp Asp Ser Leu Ala Ser Lys Gly Tyr Thr Lys
        195                 200                 205

Phe Val Ser Asn Pro Leu Asp Ser His Thr Val Gly Asp Pro Tyr Thr
    210                 215                 220

Asp Tyr Glu Lys Ala Ala Arg Asp Leu Asp Leu Ser Asn Ala Lys Glu
225                 230                 235                 240

Thr Phe Asn Pro Leu Val Ala Ala Xaa Pro Ser Val Asn Val Ser Met
                245                 250                 255

Glu Lys Val Ile Leu Ser Pro Asn Glu Asn Leu Ser Asn Ser Val Glu
            260                 265                 270

Ser His Ser Ser Thr Asn Trp Ser Tyr Thr Asn Thr Glu Gly Ala Ser
        275                 280                 285

Ile Glu Ala Gly Gly Gly Pro Leu Gly Leu Ser Phe Gly Val Ser Val
    290                 295                 300

Asn Tyr Gln His Ser Glu Thr Val Ala Gln Glu Trp Gly Thr Ser Thr
305                 310                 315                 320

Gly Asn Thr Ser Gln Phe Asn Thr Ala Ser Ala Gly Tyr Leu Asn Ala
                325                 330                 335

Asn Ile Arg Tyr
            340
```

(2) INFORMATION FOR SEQ ID NO:11:

(i) SEQUENCE CHARACTERISTICS:
(A) LENGTH: 1341 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: PS177C8a (xi) SEQUENCE DESCRIPTION: SEQ ID NO:11:

```
ATGTTTATGG TTTCTAAAAA ATTACAAGTA GTTACTAAAA CTGTATTGCT TAGTACAGTT      60

TTCTCTATAT CTTTATTAAA TAATGAAGTG ATAAAAGCTG AACAATTAAA TATAAATTCT     120

CAAAGTAAAT ATACTAACTT GCAAAATCTA AAAATCACTG ACAAGGTAGA GGATTTTAAA     180

GAAGATAAGG AAAAAGCGAA AGAATGGGGG AAAGAAAAAG AAAAAGAGTG GAAACTAACT     240

GCTACTGAAA AAGGAAAAAT GAATAATTTT TTAGATAATA AAAATGATAT AAAGACAAAT     300

TATAAAGAAA TTACTTTTTC TATGGCAGGC TCATTTGAAG ATGAAATAAA AGATTTAAAA     360

GAAATTGATA AGATGTTTGA TAAAACCAAT CTATCAAATT CTATTATCAC CTATAAAAAT     420
```

-continued

GTGGAACCGA CAACAATTGG ATTTAATAAA TCTTTAACAG AAGGTAATAC GATTAATTCT 480

GATGCAATGG CACAGTTTAA AGAACAATTT TTAGATAGGG ATATTAAGTT TGATAGTTAT 540

CTAGATACGC ATTTAACTGC TCAACAAGTT TCCAGTAAAG AAAGAGTTAT TTTGAAGGTT 600

ACGGTTCCGA GTGGGAAAGG TTCTACTACT CCAACAAAAG CAGGTGTCAT TTTAAATAAT 660

AGTGAATACA AAATGCTCAT TGATAATGGG TATATGGTCC ATGTAGATAA GGTATCAAAA 720

GTGGTGAAAA AAGGGGTGGA GTGCTTACAA ATTGAAGGGA CTTTAAAAAA GAGTCTTGAC 780

TTTAAAAATG ATATAAATGC TGAAGCGCAT AGCTGGGGTA TGAAGAATTA TGAAGAGTGG 840

GCTAAAGATT TAACCGATTC GCAAAGGGAA GCTTTAGATG GGTATGCTAG GCAAGATTAT 900

AAAGAAATCA ATAATTATTT AAGAAATCAA GGCGGAAGTG GAAATGAAAA ACTAGATGCT 960

CAAATAAAAA ATATTTCTGA TGCTTTAGGG AAGAAACCAA TACCGGAAAA TATTACTGTG 1020

TATAGATGGT GTGGCATGCC GGAATTTGGT TATCAAATTA GTGATCCGTT ACCTTCTTTA 1080

AAAGATTTTG AAGAACAATT TTTAAATACA ATCAAAGAAG ACAAAGGATA TATGAGTACA 1140

AGCTTATCGA GTGAACGTCT TGCAGCTTTT GGATCTAGAA AAATTATATT ACGATTACAA 1200

GTTCCGAAAG GAAGTACGGG TGCGTATTTA AGTGCCATTG GTGGATTTGC AAGTGAAAAA 1260

GAGATCCTAC TTGATAAAGA TAGTAAATAT CATATTGATA AAGTAACAGA GGTAATTATT 1320

AAGGTGTTAA GCGATATGTA G 1341

(2) INFORMATION FOR SEQ ID NO:12:

(i) SEQUENCE CHARACTERISTICS:
(A) LENGTH: 446 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: PS177C8a (xi) SEQUENCE DESCRIPTION: SEQ ID NO:12:

```
Met Phe Met Val Ser Lys Lys Leu Gln Val Val Thr Lys Thr Val Leu
1               5                   10                  15

Leu Ser Thr Val Phe Ser Ile Ser Leu Leu Asn Asn Glu Val Ile Lys
            20                  25                  30

Ala Glu Gln Leu Asn Ile Asn Ser Gln Ser Lys Tyr Thr Asn Leu Gln
        35                  40                  45

Asn Leu Lys Ile Thr Asp Lys Val Glu Asp Phe Lys Glu Asp Lys Glu
    50                  55                  60

Lys Ala Lys Glu Trp Gly Lys Glu Lys Glu Lys Glu Trp Lys Leu Thr
65                  70                  75                  80

Ala Thr Glu Lys Gly Lys Met Asn Asn Phe Leu Asp Asn Lys Asn Asp
                85                  90                  95

Ile Lys Thr Asn Tyr Lys Glu Ile Thr Phe Ser Met Ala Gly Ser Phe
            100                 105                 110

Glu Asp Glu Ile Lys Asp Leu Lys Glu Ile Asp Lys Met Phe Asp Lys
        115                 120                 125

Thr Asn Leu Ser Asn Ser Ile Ile Thr Tyr Lys Asn Val Glu Pro Thr
    130                 135                 140

Thr Ile Gly Phe Asn Lys Ser Leu Thr Glu Gly Asn Thr Ile Asn Ser
145                 150                 155                 160
```

-continued

```
Asp Ala Met Ala Gln Phe Lys Glu Gln Phe Leu Asp Arg Asp Ile Lys
                165                 170                 175

Phe Asp Ser Tyr Leu Asp Thr His Leu Thr Ala Gln Gln Val Ser Ser
            180                 185                 190

Lys Glu Arg Val Ile Leu Lys Val Thr Val Pro Ser Gly Lys Gly Ser
        195                 200                 205

Thr Thr Pro Thr Lys Ala Gly Val Ile Leu Asn Asn Ser Glu Tyr Lys
    210                 215                 220

Met Leu Ile Asp Asn Gly Tyr Met Val His Val Asp Lys Val Ser Lys
225                 230                 235                 240

Val Val Lys Lys Gly Val Glu Cys Leu Gln Ile Glu Gly Thr Leu Lys
                245                 250                 255

Lys Ser Leu Asp Phe Lys Asn Asp Ile Asn Ala Glu Ala His Ser Trp
            260                 265                 270

Gly Met Lys Asn Tyr Glu Glu Trp Ala Lys Asp Leu Thr Asp Ser Gln
        275                 280                 285

Arg Glu Ala Leu Asp Gly Tyr Ala Arg Gln Asp Tyr Lys Glu Ile Asn
    290                 295                 300

Asn Tyr Leu Arg Asn Gln Gly Gly Ser Gly Asn Glu Lys Leu Asp Ala
305                 310                 315                 320

Gln Ile Lys Asn Ile Ser Asp Ala Leu Gly Lys Lys Pro Ile Pro Glu
                325                 330                 335

Asn Ile Thr Val Tyr Arg Trp Cys Gly Met Pro Glu Phe Gly Tyr Gln
            340                 345                 350

Ile Ser Asp Pro Leu Pro Ser Leu Lys Asp Phe Glu Glu Gln Phe Leu
        355                 360                 365

Asn Thr Ile Lys Glu Asp Lys Gly Tyr Met Ser Thr Ser Leu Ser Ser
    370                 375                 380

Glu Arg Leu Ala Ala Phe Gly Ser Arg Lys Ile Ile Leu Arg Leu Gln
385                 390                 395                 400

Val Pro Lys Gly Ser Thr Gly Ala Tyr Leu Ser Ala Ile Gly Gly Phe
                405                 410                 415

Ala Ser Glu Lys Glu Ile Leu Leu Asp Lys Asp Ser Lys Tyr His Ile
            420                 425                 430

Asp Lys Val Thr Glu Val Ile Ile Lys Val Leu Ser Asp Met
        435                 440                 445
```

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GCTGATGAAC CATTTAATGC C 21

(2) INFORMATION FOR SEQ ID NO:14:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO:14:

CTCTTTAAAG TAGATACTAA GC 22

(2) INFORMATION FOR SEQ ID NO:15:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

GATGAGAACT TATCAAATAG TATC 24

(2) INFORMATION FOR SEQ ID NO:16:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

CGAATTCTTT ATTAGATAAG CAACAACAAA CCT 33

(2) INFORMATION FOR SEQ ID NO:17:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

GTTATTTCGC AAAAAGGCCA AAAG 24

(2) INFORMATION FOR SEQ ID NO:18:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

GAATATCAAT CTGATAAAGC GTTAAACCCA G 31

(2) INFORMATION FOR SEQ ID NO:19:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

GCAGCYTGTT TAGCAATAAA AGT 23

-continued (2) INFORMATION FOR SEQ ID NO:20:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

CAAAGGAAGA GTAGCTGTTA 20

(2) INFORMATION FOR SEQ ID NO:21:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

CAATGTTAGC TTGGAAAATG TCACC 25

(2) INFORMATION FOR SEQ ID NO:22:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

GCTTAGTATC TACTTTAAAG AG 22

(2) INFORMATION FOR SEQ ID NO:23:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

GATACTATTT GATAAGTTCT CATC 24

(2) INFORMATION FOR SEQ ID NO:24:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:24:

CTTTTGGCCT TTTTGCGAAA TAAC 24

(2) INFORMATION FOR SEQ ID NO:25:

-continued (i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:25:

CTGGGTTTAA CGCTTTATCA GATTGATATT C 31

(2) INFORMATION FOR SEQ ID NO:26:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:26:

ACTTTTATTG CTAAACARGC TGC 23

(2) INFORMATION FOR SEQ ID NO:27:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:27:

TAACAGCTAC TCTTCCTTTG 20

(2) INFORMATION FOR SEQ ID NO:28:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:28:

GGTGACATTT TCCAAGCTAA CATTG 25

(2) INFORMATION FOR SEQ ID NO:29:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:29:

CCAGTCCAAT GAACCTCTTA C 21

(2) INFORMATION FOR SEQ ID NO:30:

(i) SEQUENCE CHARACTERISTICS:
(A) LENGTH: 21 base pairs
(B) TYPE: nucleic acid
(C) STRANDEDNESS: single -continued (D) TOPOLOGY: linear (ii) MOLECULE TYPE: DNA (genomic)

(xi) SEQUENCE DESCRIPTION: SEQ ID NO:30:

AGGGAACAAA CCTTCCCAAC C 21

(2) INFORMATION FOR SEQ ID NO:31:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:31:

CARMTAKTAA MTAGGGATAG 20

(2) INFORMATION FOR SEQ ID NO:32:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:32:

AGYTTCTATC GAAGCTGGGR ST 22

(2) INFORMATION FOR SEQ ID NO:33:

(i) SEQUENCE CHARACTERISTICS:
(A) LENGTH: 1035 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:33:

GGGTTAATTG GGTATTATTT TAAAGGGAAA GATTTTAATA ATCTGACTAT GTTTGCACCA 60

ACCATAAATA ATACGCTTAT TTATGATCGG CAAACAGCAG ATACACTATT AAATAAGCAG 120

CAACAAGAGT TCAATTCTAT TCGATGGATT GGTTTAATAC AAAGTAAAGA AACAGGTGAC 180

TTTACATTCC AATTATCAGA TGATAAAAAT GCCATCATTG AAATAGATGG AAAAGTTGTT 240

TCTCGTAGAG GAGAAGATAA ACAAACTATC CATTTAGAAA AAGGAAAGAT GGTTCCAATC 300

AAAATTGAGT ACCAGTCCAA TGAACCTCTT ACTGTAGATA GTAAAGTATT TAACGATCTT 360

AAACTATTTA AAATAGATGG TCATAATCAA TCGCATCAAA TACAGCAAGA TGATTTGAAA 420

ATCCTGAATT TAATAAAAAG GAAACGAAAG AGCTTTTATC AAAAACAGCA AAAAGAACCT 480

TTTCTCTTCA AAACGGGGTT GAGAAGCGAT GAGGATGATG ATCTAGGATA CAGATGGTGA 540

TAGCATTCCT GGATAATTGG GAAATGAATG GATATACCAT TCAAACGAAA AATGGCAGTC 600

AAATGGGATG ATTCATTTGC AGAAAAAGGA TATACAAAAT TTGTTTCGAA TCCATATGAA 660

GCCCATACAG CAGGAGATCC TTATACCGAT TATGAAAAAG CAGCAAAAGA TATTCCTTTA 720

TCGAACGCAA AAGAAGCCTT TAATCCTCTT GTAGCTGCTT TTCCATCTGT CAATGTAGGA 780

TTAGAAAAAG TAGTAATTTC TAAAAATGAG GATATGAGTC AGGGTGTATC ATCCAGCACT 840

-continued

```
TCGAATAGTG CCTCTAATAC AAATTCAATT GGTGTTACCG TAGATGCTGG TTGGGAAGGT    900

TTGTTCCCTA AATTTGGTAT TTCAACTAAT TATCAAAACA CATGGACCAC TGCACAAGAA    960

TGGGGCTCTT CTAAAGAAGA TTCTACCCAT ATAAATGGAG CACAATCAGC CTTTTTAAAT   1020

GCAAATGTAC GATAT                                                    1035
```

(2) INFORMATION FOR SEQ ID NO:34:

(i) SEQUENCE CHARACTERISTICS:
(A) LENGTH: 345 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:34:

```
Gly Leu Ile Gly Tyr Tyr Phe Lys Gly Lys Asp Phe Asn Asn Leu Thr
1               5                   10                  15

Met Phe Ala Pro Thr Ile Asn Asn Thr Leu Ile Tyr Asp Arg Gln Thr
            20                  25                  30

Ala Asp Thr Leu Leu Asn Lys Gln Gln Gln Glu Phe Asn Ser Ile Arg
        35                  40                  45

Trp Ile Gly Leu Ile Gln Ser Lys Glu Thr Gly Asp Phe Thr Phe Gln
    50                  55                  60

Leu Ser Asp Asp Lys Asn Ala Ile Ile Glu Ile Asp Gly Lys Val Val
65                  70                  75                  80

Ser Arg Arg Gly Glu Asp Lys Gln Thr Ile His Leu Glu Lys Gly Lys
                85                  90                  95

Met Val Pro Ile Lys Ile Glu Tyr Gln Ser Asn Glu Pro Leu Thr Val
            100                 105                 110

Asp Ser Lys Val Phe Asn Asp Leu Lys Leu Phe Lys Ile Asp Gly His
        115                 120                 125

Asn Gln Ser His Gln Ile Gln Gln Asp Asp Leu Lys Ile Leu Asn Leu
    130                 135                 140

Ile Lys Arg Lys Arg Lys Ser Phe Tyr Gln Lys Gln Gln Lys Glu Pro
145                 150                 155                 160

Phe Leu Phe Lys Thr Gly Leu Arg Ser Asp Glu Asp Asp Asp Leu Gly
                165                 170                 175

Tyr Arg Trp Xaa Xaa His Ser Trp Ile Ile Gly Lys Xaa Met Asp Ile
            180                 185                 190

Pro Phe Lys Arg Lys Met Ala Val Lys Trp Asp Asp Ser Phe Ala Glu
        195                 200                 205

Lys Gly Tyr Thr Lys Phe Val Ser Asn Pro Tyr Glu Ala His Thr Ala
    210                 215                 220

Gly Asp Pro Tyr Thr Asp Tyr Glu Lys Ala Ala Lys Asp Ile Pro Leu
225                 230                 235                 240

Ser Asn Ala Lys Glu Ala Phe Asn Pro Leu Val Ala Ala Phe Pro Ser
                245                 250                 255

Val Asn Val Gly Leu Glu Lys Val Val Ile Ser Lys Asn Glu Asp Met
            260                 265                 270

Ser Gln Gly Val Ser Ser Ser Thr Ser Asn Ser Ala Ser Asn Thr Asn
        275                 280                 285

Ser Ile Gly Val Thr Val Asp Ala Gly Trp Glu Gly Leu Phe Pro Lys
    290                 295                 300

Phe Gly Ile Ser Thr Asn Tyr Gln Asn Thr Trp Thr Thr Ala Gln Glu
```

-continued

```
305                 310                 315                 320

Trp Gly Ser Ser Lys Glu Asp Ser Thr His Ile Asn Gly Ala Gln Ser
                325                 330                 335

Ala Phe Leu Asn Ala Asn Val Arg Tyr
            340                 345
```

(2) INFORMATION FOR SEQ ID NO:35:

(i) SEQUENCE CHARACTERISTICS:
(A) LENGTH: 1037 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

```
GGGTTAATTG GGTATTATTT TAAAGGGAAA GATTTTAATA ATCTGACTAT GTTTGCACCA     60

ACCATAAATA ATACGCTTAT TTATGATCGG CAAACAGCAG ATACACTATT AAATAAGCAG    120

CAACAAGAGT TCAATTCTAT TCGATGGATT GGTTTAATAC AAAGTAAAGA AACAGGTGAC    180

TTTACATTCC AATTATCAGA TGATAAAAAT GCCATCATTG AAATAGATGG AAAAGTTGTT    240

TCTCGTAGAG GAGAAGATAA ACAAACTATC CATTTAGAAA AAGGAAAGAT GGTTCCAATC    300

AAAATTGAGT ACCAGTCCAA TGAACCTCTT ACTGTAGATA GTAAAGTATT TAACGATCTT    360

AAACTATTTA AAATAGATGG TCATAATCAA TCGCATCAAA TACAGCAAGA TGATTTGAAA    420

AATCCTGAAT TTAATAAAAA AGAAACGAAA GAGCTTTTAT CAAAAACAGC AAAAAGRAAC    480

CTTTTCTCTT CAAACGRRGT KGAGAAGCGA TGAGGATGAT RATCYTAGAT ACAGGTGGKG    540

ATAGCATTCC YKGATAATTG GGGAAATGAA WGGRTATACC ATTCAACSGA AAAATGGSAG    600

TCAAATGGGA TGATTCATTT GCGGAAAAAG GATATACAAA ATTTGTTTCG AATCCATATG    660

AAGCCCATAC AGCAGGAGAT CCTTATACCG ATTATGAAAA AGCAGCAAAA GATATTCCTT    720

TATCGAACGC AAAAGAAGCC TTTAATCCTC TTGTAGCTGC TTTTCCATCT GTCAATGTAG    780

GATTAGAAAA AGTAGTAATT TCTAAAAATG AGGATATGAG TCAGGGTGTA TCATCCAGCA    840

CTTCGAATAG TGCCTCTAAT ACAAATTCAA TTGGTGTTAC CGTAGATGCT GGTTGGGAAG    900

GTTTGTTCCC TAAATTTGGT ATTTCAACTA ATTATCAAAA CACATGGACC ACTGCACAAG    960

AATGGGGCTC TTCTAAAGAA GATTCTACCC ATATAAATGG AGCACAATCA GCCTTTTTAA   1020

ATGCAAATGT ACGATAT                                                  1037
```

(2) INFORMATION FOR SEQ ID NO:36:

(i) SEQUENCE CHARACTERISTICS:
(A) LENGTH: 1048 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

```
TGGGTTAATT GGGTATTATT TTAAAGGGCA AGAGTTTAAT CATCTTACTT TGTTCGCACC     60

AACACGTGAT AATACCCTTA TTTATGATCA ACAAACAGCG AATTCCTTAT TAGATACCAA    120

GCAACAAGAA TATCAATCTA TTCGCTGGAT TGGTTTAATT CAAAGTAAAG AAACGGGTGA    180

TTTCACATTT AACTTATCAG ATGATCAACA TGCAATTATA GAAATCGATG GCAAAATCAT    240

TTCGCATAAA GGACAGAATA AACAAGTTGT TCACTTAGAA AAAGGAAAGT TAGTCCCGAT    300
```

-continued

AAAAATTGAG TATCAATCAG ATCAACTATT AAATAGGGAT AGTAACATCT TTAAAGAGTT 360

TAAATTATTC AAAGTAGATA GTCAGCAACA CGCTCACCAA GTTCAACTAG ACGAATTAAG 420

AAACCCTGCG TTTAATAAAA AGGAAACACA ACAATCTTAA GAAAAAGCAT CCAAAAACAA 480

TCTTTTTACA CCAGGGACAT TAAAAGGAAG ATACTGATGA TGATGATAAG GATAACAGGA 540

TGGGAGATTC TATTCCTGGA CCTTTTGGGG GAAGAAAATG GGTATACCAA TCCCAAAATA 600

AAATAGCTGG TCCAAGTGGG ATGTTCATTC GCCGCGAAAG GGTATACAAA TTTGTTTCTT 660

AATCCACTTG ATAGTCATAC AGTTGGAGAT CCCTATACGG ATTATGAAAA AGCAGCAAGA 720

GATTTAGACT TGGCCCAATG CAAAAGAAAC ATTTAACCCA TTAGTAGCTG CTTTTCCAAG 780

TGTGAATGTG AATTTGGAAA AAGTCATTTT ATCTAAAGAT GAAAATCTAT CCAATAGTGT 840

AGAGTCACAT TCCTCCACCA ACTGGTCTTA TACGAATACA GAAGGAGCTT CTATCGAAGC 900

TGGGGCTAAA CCAGAGGGTC CTACTTTTGG AGTGAGTGCT ACTTATCAAC ACTCTGAAAC 960

AGTTGCAAAA GAATGGGGAA CATCTACAGG AAATACCTCG CAATTTAATA CAGCTTCAGC 1020

AGGATATTTA AATGCAAATG TACGATAT 1048

(2) INFORMATION FOR SEQ ID NO:37:

(i) SEQUENCE CHARACTERISTICS:
(A) LENGTH: 1175 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

ACCTCTAGAT GCANGCTCGA GCGGCCGCCA GTGTGATGGA TATCTGCAGA ATTCGGATTA 60

CTTGGGTATT ATTTTAAAGG GAAAGAGTTT AATCATCTTA CTTTGTTCGC ACCAACACGT 120

GATAATACCC TTATTTATGA TCAACAAACA GCGAATTCCT TATTAGATAC CAAACAACAA 180

GAATATCAAT CTATTCGCTG GATTGGTTTG ATTCAAAGTA AAGAAACAGG TGATTTCACG 240

TTTAACTTAT CTGATGATCA AAATGCAATT ATAGAAATAG ATGGCAAAAT CATTTCGCAT 300

AAAGGACAGA ATAAACAAGT TGTTCACTTA GAAAAAGGAA AGTTAGTCCC GATAAAAATT 360

GAGTATCAAT CAGATCAGAT ATTAACTAGG GATAGTAACA TCTTTAAAGA GTTCAATTAT 420

TCAAAGTAGA TAGTCAAGCA ACACTCTCAC CAAAGTTCAA CTTAGGNCNG AATTAAGNAA 480

CCCTNGGATT TTAANTTNAA AAAAAGGAAC CCNCANCATT CTTTAGGAAA AAGCAGCAAN 540

AACCAAATCC TTTTTTACCA CAGGATATTG AAAAGGAGAT ACGGGNTNGA TGATGGATTG 600

ATACCGGGAT ACCAGTTGGG GNTTCTANTC CCTGACCTTT GGGGAAAGAA AATNGGTATA 660

CCNATCCCAA AANTTAAGCC AGCTGTCCAG GTGGGATGAT TCAATTCGCC CGCGAAAGGG 720

TATACCAAAA TTTGTTTCTT AATCCACTTG AGAGTCATAC AGTTGGAGAT CCCTATACGG 780

ATTATGAAAA AGCAGCAAGA GATTTAGACT TGGCCAATGC AAAAGAAACA TTTAACCCAT 840

TAGTAGCTGC TTTTCCAAGT GTGAATGTGA ATTTGGAAAA AGTAATATTA TCCCCAGATG 900

AGAATTTATC TAACAGTGTA GAATCTCATT CGTCTACAAA TTGGTCTTAT ACGAATACTG 960

AAGGAGCTTC TATCGAAGCT GGGGGTGGTC CATTAGGTAT TTCATTTGGA GTGAGTGCTA 1020

ATTATCAACA CTCTGAAACA GTTGCAAAAG AATGGGGAAC ATCTACAGGA AATACCTCGC 1080

AATTTAATAC AGCTTCAGCA GGATATTTAA ATGCCAATGG TCGATNTAAG CCGAATNCCA 1140

NCACACTGNC GGCCGTTAGT AGTGGCACCG AGCCC 1175

(2) INFORMATION FOR SEQ ID NO:38:

(i) SEQUENCE CHARACTERISTICS:
(A) LENGTH: 1030 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

```
GGRTTAMTTG GGTATTATTT TAAAGGGAAA GATTTTAATG ATCTTACTGT ATTTGCACCA     60
ACGCGTGGGA ATACTCTTGT ATATGATCAA CAAACAGCAA ATACATTACT AAATCAAAAA    120
CAACAAGACT TTCAGTCTAT TCGTTGGGTT GGTTTAATTC AAAGTAAAGA AGCAGGCGAT    180
TTTACATTTA ACTTATCAGA TGATGAACAT ACGATGATAG AAATCGATGG GAAAGTTATT    240
TCTAATAAAG GGAAAGAAAA ACAAGTTGTC CATTTAGAAA AAGGACAGTT CGTTTCTATC    300
AAAATAGAAT ATCAAGCTGA TGAACCATTT AATGCGGATA GTCAAACCTT TAAAAATTTG    360
AAACTCYTTA AAGTAGATAC TAAGCAACAG TCCCAGCAAA TTCAACTAGA TGAATTAAGA    420
AACCCTGRAA TTTAATAAAA AAGAAACACA AGAATTTCTA ACAAAAGCAA CAAAAACAAA    480
CCTTATTACT CAAAAAGTGA AGAGTACTAG GGATGAAGAC ACGGATACAG ATGGAGATTC    540
TATTCCAGAC ATTTGGGAAG AAAATGGGTA TACCATCCAA AATAAGATTG CCGTCAAATG    600
GGATGATTCA TTAGCAAGTA AAGGATATAC GAAATTTGTT TCAAACCCAC TAGATACTCA    660
CACGGTTGGA GATCCTTATA CAGATTATGA AAAAGCAGCA AGGGATTTAG ATTTGTCAAA    720
TGCAAAAGAA ACATTTAACC CATTAGTTGC GGCTTTTCCA AGTGTGAATG TGAGTATGGA    780
AAAAGTGATA TTGTCTCCAG ATGAGAACTT ATCAAATAGT ATCGAGTCTC ATTCATCTAC    840
GAATTGGTCG TATACGAATA CAGAAGGGGC TTCTATTGAA GCTGGTGGGG GAGCATTAGG    900
CCTATCTTTT GGTGTAAGTG CAAACTATCA ACATTCTGAA ACAGTTGGGT ATGAATGGGG    960
AACATCTACG GGAAATACTT CGCAATTTAA TACAGCTTCA GCGGGGTATT TAAATGCCAA   1020
TRTAMGATAT                                                          1030
```

(2) INFORMATION FOR SEQ ID NO:39:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:39:

```
CACTCAAAAA ATGAAAAGGG AAA                                             23
```

(2) INFORMATION FOR SEQ ID NO:40:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:40:

```
CCGGTTTTAT TGATGCTAC                                                  19
```

-continued (2) INFORMATION FOR SEQ ID NO:41:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:41:

AGAACAATTT TTAGATAGGG 20

(2) INFORMATION FOR SEQ ID NO:42:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:42:

TCCCTAAAGC ATCAGAAATA 20

(2) INFORMATION FOR SEQ ID NO:43:

(i) SEQUENCE CHARACTERISTICS:
(A) LENGTH: 1170 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:43:

ATGAAGAAAC AAATAGCAAG CGTTGTAACT TGTACGCTAT TAGCCCCTAT GCTTTTTAAT 60

GGAGATATGA ACGCTGCTTA CGCAGCTAGT CAAACAAAAC AAACACCTGC AGCTCAGGTA 120

AACCAAGAGA AAGAAGTAGA TCGAAAAGGA TTACTTGGCT ATTACTTTAA AGGGAAAGAT 180

TTTAATGATC TTACTGTATT TGCACCAACG CGTGGGAATA CTCTTGTATA TGATCAACAA 240

ACAGCAAATA CATTACTAAA TCAAAAACAA CAAGACTTTC AGTCTATTCG TTGGGTTGGT 300

TTAATTCAAA GTAAAGAAGC AGGCGATTTT ACATTTAACT TATCAGATGA TGAACATACG 360

ATGATAGAAA TCGATGGGAA AGTTATTTCT AATAAAGGGA AAGAAAAACA AGTTGTCCAT 420

TTAGAAAAAG GACAGTTCGT TTCTATAAAA TGATTCAGCT GATGAACCAT TTAATGCGGT 480

AGTAAACCTT TAAAAATTTG AAACTCTTTA AAGTAGATAC TAAGCAACAG TCCCAGCAAA 540

TTCAACTAGA TGAATTAAGA AACCCTGAAT TTAATAAAAA AGAAACACAA GAATTTCTAA 600

CAAAAGCAAC AAAAACAAAC CTTATTACTC AAAAAGTGAA GAGTACTAGG GATGAAGACA 660

CGGATACAGA TGGAGATTCT ATTCCAGACA TTTGGGAAGA AAATGGGTAT ACCATCCAAA 720

ATAAATTGCC GTCAAATGGG ATGATTCATT AGCAAGTAAA GGATATACGA AATTTGTTTC 780

AAACCCACTA GATACTCACA CGGTTGGAGA TCCTTATACA GATTATGAAA AAGCAGCAAG 840

GGATTTAGAT TTGTCAAATG CAAAAGAAAC ATTTAACCCA TTAGTTGCGG CTTTTCCAAG 900

TGTAATTGAG TATGGAAAAA GGATTTGTTC CAGATGAGAA CTTATCAAAT AGTATCGAGT 960

TCATTCATTC CTACAATTGG TCGATACGAA TACAGAAGGG GCTTCTATTG AAGCTGGTGG 1020

GGGAGCATTA GGCCTATCTT TTGGTGTAAG TGCAAACTAT CAACATTCTG AAACAGTTGG 1080

-continued

GTATGAATGG GGAACATCTA CGGGAAATAC TTCGCAATTT AATACAGCTT CAGCGGGGTA 1140

TTTAAATGCG AATGTTGCTA CAATAACGTG 1170

(2) INFORMATION FOR SEQ ID NO:44:

(i) SEQUENCE CHARACTERISTICS:
(A) LENGTH: 348 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:44:

```
Met Lys Lys Gln Ile Ala Ser Val Val Thr Cys Thr Leu Leu Ala Pro
1               5                   10                  15

Met Leu Phe Asn Gly Asp Met Asn Ala Ala Tyr Ala Ala Ser Gln Thr
            20                  25                  30

Lys Gln Thr Pro Ala Ala Gln Val Asn Gln Glu Lys Glu Val Asp Arg
        35                  40                  45

Lys Gly Leu Leu Gly Tyr Tyr Phe Lys Gly Lys Asp Phe Asn Asp Leu
    50                  55                  60

Thr Val Phe Ala Pro Thr Arg Gly Asn Thr Leu Val Tyr Asp Gln Gln
65                  70                  75                  80

Thr Ala Asn Thr Leu Leu Asn Gln Lys Gln Gln Asp Phe Gln Ser Ile
                85                  90                  95

Arg Trp Val Gly Leu Ile Gln Ser Lys Glu Ala Gly Asp Phe Thr Phe
            100                 105                 110

Asn Leu Ser Asp Asp Glu His Thr Met Ile Glu Ile Asp Gly Lys Val
        115                 120                 125

Ile Ser Asn Lys Gly Lys Glu Lys Gln Val Val His Leu Glu Lys Gly
    130                 135                 140

Gln Phe Val Ser Xaa Lys Xaa Xaa Xaa Xaa Ala Asp Glu Pro Phe Asn
145                 150                 155                 160

Ala Xaa Ser Xaa Thr Phe Lys Asn Leu Lys Leu Phe Lys Val Asp Thr
                165                 170                 175

Lys Gln Gln Ser Gln Gln Ile Gln Leu Asp Glu Leu Arg Asn Pro Glu
            180                 185                 190

Phe Asn Lys Lys Glu Thr Gln Glu Phe Leu Thr Lys Ala Thr Lys Thr
        195                 200                 205

Asn Leu Ile Thr Gln Lys Val Lys Ser Thr Arg Asp Glu Asp Thr Asp
    210                 215                 220

Thr Asp Gly Asp Ser Ile Pro Asp Ile Trp Glu Glu Asn Gly Tyr Thr
225                 230                 235                 240

Ile Gln Asn Xaa Ile Ala Val Lys Trp Asp Asp Ser Leu Ala Ser Lys
                245                 250                 255

Gly Tyr Thr Lys Phe Val Ser Asn Pro Leu Asp Thr His Thr Val Gly
            260                 265                 270

Asp Pro Tyr Thr Asp Tyr Glu Lys Ala Ala Arg Asp Leu Asp Leu Ser
        275                 280                 285

Asn Ala Lys Glu Thr Phe Asn Pro Leu Val Ala Ala Phe Pro Ser Val
    290                 295                 300

Asn Xaa Ser Met Glu Lys Xaa Ile Leu Xaa Pro Asp Glu Asn Leu Ser
305                 310                 315                 320

Asn Ser Ile Glu Xaa His Ser Phe Leu Xaa Ile Gly Arg Ile Arg Ile
```

-continued

```
            325                 330                 335

Gln Lys Gly Leu Leu Leu Lys Leu Val Gly Glu His
            340                 345
```

(2) INFORMATION FOR SEQ ID NO:45:

(i) SEQUENCE CHARACTERISTICS:
(A) LENGTH: 3 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:45:

```
ATG                                                                        3
```

(2) INFORMATION FOR SEQ ID NO:46:

(i) SEQUENCE CHARACTERISTICS:
(A) LENGTH: 1 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:46:

```
Met
1
```

(2) INFORMATION FOR SEQ ID NO:47:

(i) SEQUENCE CHARACTERISTICS:
(A) LENGTH: 2583 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:47:

```
ATGACATATA TGAAAAAAAA GTTAGTTAGT GTTGTAACTT GCACGTTATT GGCTCCGATA      60

TTTTTGACTG GAAATGTACA TCCTGTTAAT GCAGACAGTA AAAAAAGTCA GCCTTCTACA     120

GCGCAGGAAA AACAAGAAAA GCCGGTTGAT CGAAAAGGGT TACTCGGCTA TTTTTTTAAA     180

GGGAAAGAGT TTAATCATCT TACTTTGTTC GCACCAACAC GTGATAATAC CCTTATTTAT     240

GATCAACAAA CAGCGAATTC CTTATTAGAT ACCAAACAAC AAGAATATCA ATCTATTCGC     300

TGGATTGGTT TGATTCAAAG TAAAGAAACA GGTGATTTCA CGTTTAACTT ATCTGATGAT     360

CAAAATGCAA TTATAGAAAT AGATGGCAAA ATCATTTCGC ATAAAGGACA GAATAAACAA     420

GTTGTTCACT TAGAAAAAGG AAAGTTAGTC CCGATAAAAA TTGAGTATCA ATCAGATCAG     480

ATATTAACTA GGGATAGTAA CATCTTTAAA GAGTTTCAAT TATTCAAAGT AGATAGTCAG     540

CAACACTCTC ACCAAGTTCA ACTAGACGAA TTAAGAAACC CTGATTTTAA TAAAAAAGAA     600

ACACAACAAT TCTTAGAAAA AGCAGCAAAA ACAAATCTTT TTACACAGAA TATGAAAAGA     660

GATACGGATG ATGATGATGA TACGGATACA GATGGAGATT CTATTCCTGA CCTTTGGGAA     720

GAAAATGGGT ATACCATCCA AAATAAAGTA GCTGTCAAGT GGGATGATTC ATTCGCCGCG     780

AAAGGGTATA CAAAATTTGT TTCTAATCCA CTTGAGAGTC ATACAGTTGG AGATCCCTAT     840

ACGGATTATG AAAAAGCAGC AAGAGATTTA GACTTGGCCA ATGCAAAAGA AACATTTAAC     900
```

-continued

```
CCATTAGTAG CTGCTTTTCC AAGTGTGAAT GTGAATTTGG AAAAAGTAAT ATTATCCCCA    960

GATGAGAATT TATCTAACAG TGTAGAATCT CATTCGTCTA CAAATTGGTC TTATACGAAT   1020

ACTGAAGGAG CTTCTATCGA AGCTGGGGGT GGTCCATTAG GTATTTCATT TGGAGTGAGT   1080

GCTAATTATC AACACTCTGA AACAGTTGCA AAAGAATGGG GAACATCTAC AGGAAATACC   1140

TCGCAATTTA ATACAGCTTC AGCAGGATAT TTGAATGCGA ATGTTCGATA CAATAATGTG   1200

GGAACAGGTG CGATTTATGA GGTGAAACCT ACAACAAGTT TTGTATTAGA TAAAGATACT   1260

GTAGCAACAA TTACCGCAAA ATCGAATTCG ACAGCTTTAA GTATATCTCC AGGAGAAAGT   1320

TATCCCAAAA AAGGACAAAA TGGAATTGCA ATTAATACAA TGGATGATTT TAATTCCCAT   1380

CCGATTACAT TAAATAAACA ACAATTAGAT CAACTATTAA ATAATAAACC TCTTATGTTA   1440

GAAACAAATC AGGCAGATGG TGTTTATAAA ATAAAGGATA CAAGCGGTAA TATTGTGACT   1500

GGTGGAGAAT GGAACGGTGT TATCCAACAA ATTCAAGCAA AAACAGCCTC TATTATCGTT   1560

GATACGGGAG AAAGTGTTTC AGAAAAGCGT GTCGCAGCAA AAGATTATGA TAATCCTGAG   1620

GATAAAACAC CTTCTTTATC TTTAAAAGAG GCACTTAAAC TTGGATATCC AGAAGAAATT   1680

AAAGAAAAAG ATGGATTGTT GTACTATAAG GACAAGCCAA TTTACGAATC TAGTGTTATG   1740

ACTTATCTAG ATGAGAATAC AGCCAAGGAA GTGGAAAAAC AATTACAGGA TACAACCGGA   1800

ATATATAAAG ATATCAATCA TTTATATGAT GTGAAATTAA CACCTACAAT GAATTTTACG   1860

ATTAAATTAG CTTCCTTATA TGATGGAGCT GAAAATAATG ATGTGAAGAA TGGTCCTATA   1920

GGACATTGGT ATTATACCTA TAATACAGGG GGAGGAAATA CTGGAAAACA CCAATATAGG   1980

TCTGCTAATC CCAGTGCAAA TGTAGTTTTA TCTTCTGAAG CGAAAAGTAA GTTAGATAAA   2040

AATACAAATT ACTACCTTAG TATGTATATG AAAGCTGAGT CTGATACAGA GCCTACAATA   2100

GAAGTAAGTG GTGAGAATTC TACGATAACG AGTAAAAAGG TAAAACTAAA CAGTGAGGGC   2160

TATCAAAGAG TAGATATTTT AGTGCCGAAT TCTGAAAGAA ATCCAATAAA TCAAATATAT   2220

GTAAGAGGAA ATAATACAAC AAATGTATAC TGGGATGATG TTTCAATTAC AAATATTTCA   2280

GCTATAAACC CAAAAACTTT AACAGATGAA GAAATTAAAG AAATATATAA AGATTTTAGT   2340

GAGTCTAAAG ACTGGCCTTG GTTCAATGAT GTTACGTTTA AAAATATTAA ACCATTAGAG   2400

AATTATGTAA AACAATATAG AGTTGATTTC TGGAATACTA ATAGTGATAG ATCATTTAAT   2460

AGGATTAAGG ACAGTTACCC AGTTAATGAA GATGGAAGTG TTAAAGTCAA CATGACAGAA   2520

TATAATGAAG GATATCCACT TAGAATTGAA TCCGCCTACC ATTTAAATAT TTCAGATCTA   2580

TAA                                                                 2583
```

(2) INFORMATION FOR SEQ ID NO:48:

(i) SEQUENCE CHARACTERISTICS:
(A) LENGTH: 860 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:48:

```
Met Thr Tyr Met Lys Lys Lys Leu Val Ser Val Val Thr Cys Thr Leu
1               5                   10                  15

Leu Ala Pro Ile Phe Leu Thr Gly Asn Val His Pro Val Asn Ala Asp
            20                  25                  30

Ser Lys Lys Ser Gln Pro Ser Thr Ala Gln Glu Lys Gln Glu Lys Pro
        35                  40                  45
```

-continued

```
Val Asp Arg Lys Gly Leu Leu Gly Tyr Phe Phe Lys Gly Lys Glu Phe
    50                  55                  60

Asn His Leu Thr Leu Phe Ala Pro Thr Arg Asp Asn Thr Leu Ile Tyr
65                  70                  75                  80

Asp Gln Gln Thr Ala Asn Ser Leu Leu Asp Thr Lys Gln Gln Glu Tyr
                85                  90                  95

Gln Ser Ile Arg Trp Ile Gly Leu Ile Gln Ser Lys Glu Thr Gly Asp
            100                 105                 110

Phe Thr Phe Asn Leu Ser Asp Asp Gln Asn Ala Ile Ile Glu Ile Asp
        115                 120                 125

Gly Lys Ile Ile Ser His Lys Gly Gln Asn Lys Gln Val Val His Leu
    130                 135                 140

Glu Lys Gly Lys Leu Val Pro Ile Lys Ile Glu Tyr Gln Ser Asp Gln
145                 150                 155                 160

Ile Leu Thr Arg Asp Ser Asn Ile Phe Lys Glu Phe Gln Leu Phe Lys
                165                 170                 175

Val Asp Ser Gln Gln His Ser His Gln Val Gln Leu Asp Glu Leu Arg
            180                 185                 190

Asn Pro Asp Phe Asn Lys Lys Glu Thr Gln Gln Phe Leu Glu Lys Ala
        195                 200                 205

Ala Lys Thr Asn Leu Phe Thr Gln Asn Met Lys Arg Asp Thr Asp Asp
    210                 215                 220

Asp Asp Asp Thr Asp Thr Asp Gly Asp Ser Ile Pro Asp Leu Trp Glu
225                 230                 235                 240

Glu Asn Gly Tyr Thr Ile Gln Asn Lys Val Ala Val Lys Trp Asp Asp
                245                 250                 255

Ser Phe Ala Ala Lys Gly Tyr Thr Lys Phe Val Ser Asn Pro Leu Glu
            260                 265                 270

Ser His Thr Val Gly Asp Pro Tyr Thr Asp Tyr Glu Lys Ala Ala Arg
        275                 280                 285

Asp Leu Asp Leu Ala Asn Ala Lys Glu Thr Phe Asn Pro Leu Val Ala
    290                 295                 300

Ala Phe Pro Ser Val Asn Val Asn Leu Glu Lys Val Ile Leu Ser Pro
305                 310                 315                 320

Asp Glu Asn Leu Ser Asn Ser Val Glu Ser His Ser Ser Thr Asn Trp
                325                 330                 335

Ser Tyr Thr Asn Thr Glu Gly Ala Ser Ile Glu Ala Gly Gly Gly Pro
            340                 345                 350

Leu Gly Ile Ser Phe Gly Val Ser Ala Asn Tyr Gln His Ser Glu Thr
        355                 360                 365

Val Ala Lys Glu Trp Gly Thr Ser Thr Gly Asn Thr Ser Gln Phe Asn
    370                 375                 380

Thr Ala Ser Ala Gly Tyr Leu Asn Ala Asn Val Arg Tyr Asn Asn Val
385                 390                 395                 400

Gly Thr Gly Ala Ile Tyr Glu Val Lys Pro Thr Thr Ser Phe Val Leu
                405                 410                 415

Asp Lys Asp Thr Val Ala Thr Ile Thr Ala Lys Ser Asn Ser Thr Ala
            420                 425                 430

Leu Ser Ile Ser Pro Gly Glu Ser Tyr Pro Lys Lys Gly Gln Asn Gly
        435                 440                 445

Ile Ala Ile Asn Thr Met Asp Asp Phe Asn Ser His Pro Ile Thr Leu
    450                 455                 460
```

-continued

```
Asn Lys Gln Gln Leu Asp Gln Leu Leu Asn Asn Lys Pro Leu Met Leu
465                 470                 475                 480

Glu Thr Asn Gln Ala Asp Gly Val Tyr Lys Ile Lys Asp Thr Ser Gly
                485                 490                 495

Asn Ile Val Thr Gly Gly Glu Trp Asn Gly Val Ile Gln Gln Ile Gln
            500                 505                 510

Ala Lys Thr Ala Ser Ile Ile Val Asp Thr Gly Glu Ser Val Ser Glu
        515                 520                 525

Lys Arg Val Ala Ala Lys Asp Tyr Asp Asn Pro Glu Asp Lys Thr Pro
    530                 535                 540

Ser Leu Ser Leu Lys Glu Ala Leu Lys Leu Gly Tyr Pro Glu Glu Ile
545                 550                 555                 560

Lys Glu Lys Asp Gly Leu Leu Tyr Tyr Lys Asp Lys Pro Ile Tyr Glu
                565                 570                 575

Ser Ser Val Met Thr Tyr Leu Asp Glu Asn Thr Ala Lys Glu Val Glu
            580                 585                 590

Lys Gln Leu Gln Asp Thr Thr Gly Ile Tyr Lys Asp Ile Asn His Leu
        595                 600                 605

Tyr Asp Val Lys Leu Thr Pro Thr Met Asn Phe Thr Ile Lys Leu Ala
    610                 615                 620

Ser Leu Tyr Asp Gly Ala Glu Asn Asn Asp Val Lys Asn Gly Pro Ile
625                 630                 635                 640

Gly His Trp Tyr Tyr Thr Tyr Asn Thr Gly Gly Gly Asn Thr Gly Lys
                645                 650                 655

His Gln Tyr Arg Ser Ala Asn Pro Ser Ala Asn Val Val Leu Ser Ser
            660                 665                 670

Glu Ala Lys Ser Lys Leu Asp Lys Asn Thr Asn Tyr Tyr Leu Ser Met
        675                 680                 685

Tyr Met Lys Ala Glu Ser Asp Thr Glu Pro Thr Ile Glu Val Ser Gly
    690                 695                 700

Glu Asn Ser Thr Ile Thr Ser Lys Lys Val Lys Leu Asn Ser Glu Gly
705                 710                 715                 720

Tyr Gln Arg Val Asp Ile Leu Val Pro Asn Ser Glu Arg Asn Pro Ile
                725                 730                 735

Asn Gln Ile Tyr Val Arg Gly Asn Asn Thr Thr Asn Val Tyr Trp Asp
            740                 745                 750

Asp Val Ser Ile Thr Asn Ile Ser Ala Ile Asn Pro Lys Thr Leu Thr
        755                 760                 765

Asp Glu Glu Ile Lys Glu Ile Tyr Lys Asp Phe Ser Glu Ser Lys Asp
    770                 775                 780

Trp Pro Trp Phe Asn Asp Val Thr Phe Lys Asn Ile Lys Pro Leu Glu
785                 790                 795                 800

Asn Tyr Val Lys Gln Tyr Arg Val Asp Phe Trp Asn Thr Asn Ser Asp
                805                 810                 815

Arg Ser Phe Asn Arg Ile Lys Asp Ser Tyr Pro Val Asn Glu Asp Gly
            820                 825                 830

Ser Val Lys Val Asn Met Thr Glu Tyr Asn Glu Gly Tyr Pro Leu Arg
        835                 840                 845

Ile Glu Ser Ala Tyr His Leu Asn Ile Ser Asp Leu
    850                 855                 860
```

(2) INFORMATION FOR SEQ ID NO:49:

(i) SEQUENCE CHARACTERISTICS:

-continued (A) LENGTH: 1356 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:49:

```
ATGGTATCCA AAAAGTTACA ATTAGTCACA AAAACTTTAG TGTTTAGTAC AGTTTTGTCA     60

ATACCGTTAT TAAATAATAG TGAGATAAAA GCGGAACAAT TAAATATGAA TTCTCAAATT    120

AAATATCCTA ACTTCCAAAA TATAAATATC GCTGATAAGC CAGTAGATTT TAAAGAGGAT    180

AAAGAAAAAG CACGAGAATG GGGAAAAGAA AAAGAAAAAG AGTGGAAACT AACTGCTACT    240

GAAAAAGGGA AAATTAATGA TTTTTTAGAT GATAAAGATG GATTAAAAAC AAAATACAAA    300

GAAATTAATT TTTCTAAGAA TTTTGAATAT GAAACAGAGT TAAAACAGCT TGAAAAAATT    360

AATAGCATGC TAGATAAAGC AAATCTAACA AATTCAATTG TCACGTATAA AAACGTTGAG    420

CCTACAACAA TAGGATTCAA TCACTCTTTG ACTGATGGGA ATCAAATTAA TTCCGAAGCT    480

CAACAGAAGT TCAAGGAACA GTTTTTAGGA AATGATATTA AATTTGATAG TTATTTGGAT    540

ATGCACTTAA CTGAACAAAA TGTTTCCGGT AAAGAAAGGG TTATTTTAAA AGTTACAGTA    600

CTTAGTGGGA AAGGTTCTAC TCCAACAAAA GCAGGTGTTG TTTTAAATAA TAAAGAATAC    660

AAAATGTTGA TTGATAATGG ATATATACTA CATGTAGAAA ACATAACGAA AGTTGTAAAA    720

AAAGGACAGG AATGTTTACA AGTTGAAGGA ACGTTAAAAA AGAGCTTGGA CTTTAAAAAT    780

GATAGTGACG GTAAGGGAGA TTCCTGGGGA AAGAAAAATT ACAAGGAATG GTCTGATTCT    840

TTAACAAATG ATCAGAGAAA AGACTTAAAT GATTATGGTG CGCGAGGTTA TACCGAAATA    900

AATAAATATT TACGTGAAGG GGGTACCGGA AATACAGAGT TGGAGGAAAA AATTAAAAAT    960

ATTTCTGACG CACTAGAAAA GAATCCTATC CCTGAAAACA TTACTGTTTA TAGATATTGC   1020

GGAATGGCGG AATTTGGTTA TCCAATTCAA CCCGAGGCTC CCTCCGTACA AGATTTTGAA   1080

GAGAAATTTT TGGATAAAAT TAAGGAAGAA AAAGGATATA TGAGTACGAG CTTATCAAGT   1140

GATGCGACTT CTTTTGGCGC AAGAAAAATT ATCTTAAGAT TGCAGATACC AAAAGGAAGT   1200

TCAGGAGCAT ATGTAGCTGG TTTAGATGGA TTTAAACCAG CAGAGAAGGA GATTCTTATT   1260

GATAAGGGAA GCAAGTATCA TATTGATAAA GTAACAGAAG TAGTTGTGAA AGGTATTAGA   1320

AAACTCGTAG TAGATGCGAC ATTATTATTA AAATAA                             1356
```

(2) INFORMATION FOR SEQ ID NO:50:

(i) SEQUENCE CHARACTERISTICS:
(A) LENGTH: 451 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:50:

```
Met Val Ser Lys Lys Leu Gln Leu Val Thr Lys Thr Leu Val Phe Ser
1               5                   10                  15

Thr Val Leu Ser Ile Pro Leu Leu Asn Asn Ser Glu Ile Lys Ala Glu
            20                  25                  30

Gln Leu Asn Met Asn Ser Gln Ile Lys Tyr Pro Asn Phe Gln Asn Ile
        35                  40                  45

Asn Ile Ala Asp Lys Pro Val Asp Phe Lys Glu Asp Lys Glu Lys Ala
    50                  55                  60
```

-continued

```
Arg Glu Trp Gly Lys Glu Lys Glu Lys Glu Trp Lys Leu Thr Ala Thr
65                  70                  75                  80

Glu Lys Gly Lys Ile Asn Asp Phe Leu Asp Asp Lys Asp Gly Leu Lys
                85                  90                  95

Thr Lys Tyr Lys Glu Ile Asn Phe Ser Lys Asn Phe Glu Tyr Glu Thr
            100                 105                 110

Glu Leu Lys Gln Leu Glu Lys Ile Asn Ser Met Leu Asp Lys Ala Asn
        115                 120                 125

Leu Thr Asn Ser Ile Val Thr Tyr Lys Asn Val Glu Pro Thr Thr Ile
    130                 135                 140

Gly Phe Asn His Ser Leu Thr Asp Gly Asn Gln Ile Asn Ser Glu Ala
145                 150                 155                 160

Gln Gln Lys Phe Lys Glu Gln Phe Leu Gly Asn Asp Ile Lys Phe Asp
                165                 170                 175

Ser Tyr Leu Asp Met His Leu Thr Glu Gln Asn Val Ser Gly Lys Glu
            180                 185                 190

Arg Val Ile Leu Lys Val Thr Val Leu Ser Gly Lys Gly Ser Thr Pro
        195                 200                 205

Thr Lys Ala Gly Val Val Leu Asn Asn Lys Glu Tyr Lys Met Leu Ile
    210                 215                 220

Asp Asn Gly Tyr Ile Leu His Val Glu Asn Ile Thr Lys Val Val Lys
225                 230                 235                 240

Lys Gly Gln Glu Cys Leu Gln Val Glu Gly Thr Leu Lys Lys Ser Leu
                245                 250                 255

Asp Phe Lys Asn Asp Ser Asp Gly Lys Gly Asp Ser Trp Gly Lys Lys
            260                 265                 270

Asn Tyr Lys Glu Trp Ser Asp Ser Leu Thr Asn Asp Gln Arg Lys Asp
        275                 280                 285

Leu Asn Asp Tyr Gly Ala Arg Gly Tyr Thr Glu Ile Asn Lys Tyr Leu
    290                 295                 300

Arg Glu Gly Gly Thr Gly Asn Thr Glu Leu Glu Glu Lys Ile Lys Asn
305                 310                 315                 320

Ile Ser Asp Ala Leu Glu Lys Asn Pro Ile Pro Glu Asn Ile Thr Val
                325                 330                 335

Tyr Arg Tyr Cys Gly Met Ala Glu Phe Gly Tyr Pro Ile Gln Pro Glu
            340                 345                 350

Ala Pro Ser Val Gln Asp Phe Glu Glu Lys Phe Leu Asp Lys Ile Lys
        355                 360                 365

Glu Glu Lys Gly Tyr Met Ser Thr Ser Leu Ser Ser Asp Ala Thr Ser
    370                 375                 380

Phe Gly Ala Arg Lys Ile Ile Leu Arg Leu Gln Ile Pro Lys Gly Ser
385                 390                 395                 400

Ser Gly Ala Tyr Val Ala Gly Leu Asp Gly Phe Lys Pro Ala Glu Lys
                405                 410                 415

Glu Ile Leu Ile Asp Lys Gly Ser Lys Tyr His Ile Asp Lys Val Thr
            420                 425                 430

Glu Val Val Val Lys Gly Ile Arg Lys Leu Val Val Asp Ala Thr Leu
        435                 440                 445

Leu Leu Lys
    450
```

(2) INFORMATION FOR SEQ ID NO:51:

-continued (i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:51:

GCTCTAGAAG GAGGTAACTT ATGAACAAGA ATAATACTAA ATTAAGC 47

(2) INFORMATION FOR SEQ ID NO:52:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:52:

GGGGTACCTT ACTTAATAGA GACATCG 27

(2) INFORMATION FOR SEQ ID NO:53:

(i) SEQUENCE CHARACTERISTICS:
(A) LENGTH: 2364 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:53:

ATGAATATGA ATAATACTAA ATTAAACGCA AGGGCCCTAC CGAGTTTTAT TGATTATTTT 60

AATGGCATTT ATGGATTTGC CACTGGTATC AAAGACATTA TGAATATGAT TTTTAAAACG 120

GATACAGGTG GTAATCTAAC CTTAGACGAA ATCCTAAAGA ATCAGCAGTT ACTAAATGAG 180

ATTTCTGGTA AATTGGATGG GGTAAATGGG AGCTTAAATG ATCTTATCGC ACAGGGAAAC 240

TTAAATACAG AATTATCTAA GGAAATCTTA AAAATTGCAA ATGAACAGAA TCAAGTCTTA 300

AATGATGTTA ATAACAAACT CGATGCGATA AATACGATGC TTCATATATA TCTACCTAAA 360

ATCACATCTA TGTTAAGTGA TGTAATGAAG CAAAATTATG CGCTAAGTCT GCAAGTAGAA 420

TACTTAAGTA AACAATTGAA AGAAATTTCT GATAAATTAG ATGTTATTAA CGTAAATGTT 480

CTTATTAACT CTACACTTAC TGAAATTACA CCTGCATATC AACGGATTAA ATATGTAAAT 540

GAAAAATTTG AAGAATTAAC TTTTGCTACA GAAACCACTT TAAAAGTAAA AAAGGATAGC 600

TCGCCTGCTG ATATTCTTGA CGAGTTAACT GAATTAACTG AACTAGCGAA AAGTGTTACA 660

AAAAATGACG TGGATGGTTT TGAATTTTAC CTTAATACAT TCCACGATGT AATGGTAGGA 720

AATAATTTAT TCGGGCGTTC AGCTTTAAAA ACTGCTTCAG AATTAATTGC TAAAGAAAAT 780

GTGAAAACAA GTGGCAGTGA AGTAGGAAAT GTTTATAATT TCTTAATTGT ATTAACAGCT 840

CTACAAGCAA AAGCTTTTCT TACTTTAACA ACATGCCGAA AATTATTAGG CTTAGCAGAT 900

ATTGATTATA CATCTATTAT GAATGAACAT TTAAATAAGG AAAAAGAGGA ATTTAGAGTA 960

AACATCCTTC CTACACTTTC TAATACTTTT TCTAATCCTA ATTATGCAAA AGTTAAAGGA 1020

AGTGATGAAG ATGCAAAGAT GATTGTGGAA GCTAAACCAG GACATGCATT GGTTGGGTTT 1080

GAAATTAGTA ATGATTCAAT GACAGTATTA AAAGTATATG AAGCTAAGCT AAAACAAAAT 1140

TACCAAGTTG ATAAGGATTC CTTATCGGAA GTCATTTATA GTGATATGGA TAAATTATTG 1200

-continued

```
TGCCCAGATC AATCTGAACA AATTTATTAT ACAAATAATA TAGTATTTCC AAATGAATAT   1260

GTAATTACTA AAATTGATTT TACTAAGAAA ATGAAAACTT TAAGATATGA GGTAACAGCT   1320

AATTCTTACG ATTCTTCTAC AGGAGAAATT GACTTAAATA AGAAGAAAGT AGAATCAAGT   1380

GAAGCGGAGT ATAGGACGTT AAGTGCTAAT AATGATGGAG TATATATGCC GTTAGGTGTC   1440

ATCAGTGAAA CATTTTTGAC TCCAATTAAT GGATTTGGCC TCCAAGCTGA TGAAAATTCA   1500

AGATTAATTA CTTTAACATG TAAATCATAT TTAAGGGAAC TACTACTAGC GACAGACTTA   1560

AGCAATAAAG AAACTAAATT GATTGTCCCG CCTATTAGTT TTATTAGTAA TATTGTAGAA   1620

AATGGGAACT TAGAGGGAGA AAACTTAGAG CCGTGGATAG CAAATAACAA AAATGCGTAT   1680

GTAGATCATA CAGGTGGTAT AAATGGAACT AAAGTTTTAT ATGTTCATAA GGATGGTGAG   1740

TTTTCACAAT TTGTTGGAGG TAAGTTAAAA TCGAAAACAG AATATGTAAT TCAATATATT   1800

GTAAAGGGAA AAGCTTCTAT TTATTTAAAA GATAAAAAAA ATGAGAATTC CATTTATGAA   1860

GAAATAAATA ATGATTTAGA AGGTTTTCAA ACTGTTACTA AACGTTTTAT TACAGGAACG   1920

GATTCTTCAG GGATTCATTT AATTTTTACC AGTCAAAATG GCGAGGGAGC ATTTGGAGGA   1980

AACTTTATTA TCTCAGAAAT TAGGACATCC GAAGAGTTAT TAAGTCCAGA ATTGATTATG   2040

TCGGATGCTT GGGTTGGATC CCAGGGAACT TGGATCTCAG GAAATTCTCT CACTATTAAT   2100

AGTAATGTAA ATGGAACCTT TCGACAAAAT CTTCCGTTAG AAAGTTATTC AACCTATAGT   2160

ATGAACTTTA CTGTGAATGG ATTTGGCAAG GTGACAGTAA GAAATTCTCG TGAAGTATTA   2220

TTTGAAAAAA GTTATCCGCA GCTTTCACCT AAAGATATTT CTGAAAAATT TACAACTGCA   2280

GCCAATAATA CCGGATTATA TGTAGAGCTT TCTCGCTCAA CGTCGGGTGG TGCAATAAAT   2340

TTCCGAGATT TTTCAATTAA GTAA                                          2364
```

(2) INFORMATION FOR SEQ ID NO:54:

(i) SEQUENCE CHARACTERISTICS:
(A) LENGTH: 787 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:54:

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Val Glu Tyr Leu Ser Lys
```

-continued

```
    130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Met Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Ser Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ile Ser Phe Ile Ser Asn Ile Val Glu Asn Gly Asn Leu
    530                 535                 540

Glu Gly Glu Asn Leu Glu Pro Trp Ile Ala Asn Asn Lys Asn Ala Tyr
545                 550                 555                 560
```

-continued

```
Val Asp His Thr Gly Gly Ile Asn Gly Thr Lys Val Leu Tyr Val His
            565                 570                 575

Lys Asp Gly Glu Phe Ser Gln Phe Val Gly Gly Lys Leu Lys Ser Lys
        580                 585                 590

Thr Glu Tyr Val Ile Gln Tyr Ile Val Lys Gly Lys Ala Ser Ile Tyr
    595                 600                 605

Leu Lys Asp Lys Lys Asn Glu Asn Ser Ile Tyr Glu Glu Ile Asn Asn
    610                 615                 620

Asp Leu Glu Gly Phe Gln Thr Val Thr Lys Arg Phe Ile Thr Gly Thr
625                 630                 635                 640

Asp Ser Ser Gly Ile His Leu Ile Phe Thr Ser Gln Asn Gly Glu Gly
            645                 650                 655

Ala Phe Gly Gly Asn Phe Ile Ile Ser Glu Ile Arg Thr Ser Glu Glu
        660                 665                 670

Leu Leu Ser Pro Glu Leu Ile Met Ser Asp Ala Trp Val Gly Ser Gln
    675                 680                 685

Gly Thr Trp Ile Ser Gly Asn Ser Leu Thr Ile Asn Ser Asn Val Asn
    690                 695                 700

Gly Thr Phe Arg Gln Asn Leu Pro Leu Glu Ser Tyr Ser Thr Tyr Ser
705                 710                 715                 720

Met Asn Phe Thr Val Asn Gly Phe Gly Lys Val Thr Val Arg Asn Ser
            725                 730                 735

Arg Glu Val Leu Phe Glu Lys Ser Tyr Pro Gln Leu Ser Pro Lys Asp
        740                 745                 750

Ile Ser Glu Lys Phe Thr Thr Ala Ala Asn Asn Thr Gly Leu Tyr Val
    755                 760                 765

Glu Leu Ser Arg Ser Thr Ser Gly Gly Ala Ile Asn Phe Arg Asp Phe
    770                 775                 780

Ser Ile Lys
785
```

PLANTS AND CELLS TRANSFORMED WITH A NUCLEIC ACID FROM *BACILLUS THURINGIENSIS* STRAIN KB59A4-6 ENCODING A NOVEL SUP TOXIN

BACKGROUND OF THE INVENTION

Insects and other pests cost farmers billions of dollars annually in crop losses and in the expense of keeping these pests under control. The losses caused by insect pests in agricultural production environments include decrease in crop yield, reduced crop quality, and increased harvesting costs.

Cultivation methods, such as crop rotation and the application of high nitrogen levels to stimulate the growth of an adventitious root system, has partially addressed problems caused by agricultural pests. Economic demands on the utilization of farmland restrict the use of crop rotation. In addition, overwintering traits of some insects are disrupting crop rotations in some areas. Thus, chemical insecticides are relied upon most heavily to guarantee the desired level of control. Insecticides are either banded onto or incorporated into the soil.

The use of chemical insecticides has several drawbacks. Continual use of insecticides has allowed resistant insects to evolve. Situations such as extremely high populations of larvae, heavy rains, and improper calibration of insecticide application equipment can result in poor control. The use of insecticides often raises environmental concerns such as contamination of soil and of both surface and underground water supplies. The public has also become concerned about the amount of residual, synthetic chemicals which might be found on food. Working with insecticides may also pose hazards to the persons applying them. Therefore, synthetic chemical pesticides are being increasingly scrutinized, and correctly so, for their potential toxic environmental consequences. Examples of widely used synthetic chemical pesticides include the organochlorines, e.g., DDT, mirex, kepone, lindane, aldrin, chlordane, aldicarb, and dieldrin; the organophosphates, e.g., chlorpyrifos, parathion, malathion, and diazinon; and carbamates. Stringent new restrictions on the use of pesticides and the elimination of some effective pesticides from the market place could limit economical and effective options for controlling damaging and costly pests.

Because of the problems associated with the use of organic synthetic chemical pesticides, there exists a clear need to limit the use of these agents and a need to identify alternative control agents. The replacement of synthetic chemical pesticides, or combination of these agents with biological pesticides, could reduce the levels of toxic chemicals in the environment.

A biological pesticidal agent that is enjoying increasing popularity is the soil microbe *Bacillus thuringiensis* (*B.t.*). The soil microbe *Bacillus thuringiensis* (*B.t.*) is a Gram-positive, spore-forming bacterium. Most strains of *B.t.* do not exhibit pesticidal activity. Some *B.t.* strains produce, and can be characterized by, parasporal crystalline protein inclusions. These inclusions often appear microscopically as distinctively shaped crystals. Some *B.t.* proteins are highly toxic to pests, such as insects, and are specific in their toxic activity. Certain insecticidal *B.t.* proteins are associated with the inclusions. These "δ-endotoxins," are different from exotoxins, which have a non-specific host range. Other species of Bacillus also produce pesticidal proteins.

Certain Bacillus toxin genes have been isolated and sequenced, and recombinant DNA-based products have been produced and approved for use. In addition, with the use of genetic engineering techniques, new approaches for delivering these toxins to agricultural environments are under development. These include the use of plants genetically engineered with toxin genes for insect resistance and the use of stabilized intact microbial cells as toxin delivery vehicles. Thus, isolated Bacillus toxin genes are becoming commercially valuable.

Until the last fifteen years, commercial use of *B.t.* pesticides has been largely restricted to targeting a narrow range of lepidopteran (caterpillar) pests. Preparations of the spores and crystals of *B. thuringiensis* subsp.*kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *morrisoni* (a.k.a. *tenebrionis*, a.k.a. *B.t.* M-7, a.k.a. *B.t.* san diego), have been used commercially to control insects of the orders Diptera and Coleoptera, respectively. *Bacillus thuringiensis* var. *tenebrionis* has been reported to be active against two beetles in the order Coleoptera (Colorado potato beetle, *Leptinotarsa decemlineata*, and *Agelastica alni*).

More recently, new subspecies of *B.t.* have been identified, and genes responsible for active δ-endotoxin proteins have been isolated. Höfte and Whiteley classified *B.t.* crystal protein genes into four major classes (Höfte, H., H. R. Whiteley [1989] *Microbiological Reviews* 52(2) :242–255). The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. For example, CryV and CryVI have been proposed to designate a class of toxin genes that are nematode-specific.

The 1989 nomenclature and classification scheme of H öfte and Whiteley for crystal proteins was based on both the deduced amino acid sequence and the host range of the toxin. That system was adapted to cover 14 different types of toxin genes which were divided into five major classes. The number of sequenced *Bacillus thuringiensis* crystal protein genes currently stands at more than 50. A revised nomenclature scheme has been proposed which is based solely on amino acid identity (Crickmore et al. [1996] Society for Invertebrate Pathology, 29th Annual Meeting, IIIrd International Colloquium on *Bacillus thuringiensis*, University of Cordoba, Cordoba, Spain, Sep. 1–6, 1996, abstract). The mnemonic "cry" has been retained for all of the toxin genes except cytA and cytB, which remain a separate class. Roman numerals have been exchanged for Arabic numerals in the primary rank, and the parentheses in the tertiary rank have been removed. Many of the original names have been retained, with the noted exceptions, although a number have been reclassified.

Many other *B.t.* genes have now been identified. WO 94/21795, WO 96/10083, WO 98/44137, and Estruch, J. J. et al. (1996) PNAS 93:5389–5394 describe Vip1A(a), Vip1A(b), Vip2A(a), Vip2A(b), Vip3A(a), and Vip3A(b) toxins obtained from Bacillus microbes. Those toxins are reported to be produced during vegetative cell growth and were thus termed vegetative insecticidal proteins (VIP). Activity of these toxins against certain lepidopteran and certain coleopteran pests was reported. WO 98/18932 discloses new classes of pesticidal toxins.

Obstacles to the successful agricultural use of Bacillus toxins include the development of resistance to *B.t.* toxins by insects. In addition, certain insects can be refractory to the effects of Bacillus toxins. The latter includes insects such as boll weevil and black cutworm as well as adult insects of most species which heretofore have demonstrated no apparent significant sensitivity to *B.t.* δ-endotoxins. While resistance management strategies in *B.t.* transgene plant technology have become of great interest, there remains a great need for developing additional genes that can be expressed in plants in order to effectively control various insects.

The subject application provides new classes of toxins and genes, in addition to those described in WO 98/18932, and which are distinct from those disclosed in WO 94/21795, WO 96/10083, WO 98/44137, and Estruch et al.

BRIEF SUMMARY OF THE INVENTION

The subject invention concerns materials and methods useful in the control of non-mammalian pests and, particularly, plant pests. In one embodiment, the subject invention provides novel Bacillus isolates having advantageous activity against non-mammalian pests. In a further embodiment, the subject invention provides new toxins useful for the control of non-mammalian pests. In a preferred embodiment, these pests are lepidopterans and/or coleopterans. The toxins of the subject invention include δ-endotoxins as well as soluble toxins which can be obtained from the supernatant of Bacillus cultures.

The subject invention further provides nucleotide sequences which encode the toxins of the subject invention. The subject invention further provides nucleotide sequences and methods useful in the identification and characterization of genes which encode pesticidal toxins.

In one embodiment, the subject invention concerns unique nucleotide sequences which are useful as hybridization probes and/or primers in PCR techniques. The primers produce characteristic gene fragments which can be used in the identification, characterization, and/or isolation of specific toxin genes. The nucleotide sequences of the subject invention encode toxins which are distinct from previously-described toxins.

In a specific embodiment, the subject invention provides new classes of toxins having advantageous pesticidal activities. These classes of toxins can be encoded by polynucleotide sequences which are characterized by their ability to hybridize with certain exemplified sequences and/or by their ability to be amplified by PCR using certain exemplified primers.

One aspect of the subject invention pertains to the identification and characterization of entirely new families of Bacillus toxins having advantageous pesticidal properties. The subject invention includes new classes of genes and toxins referred to herein as MIS-7 and MIS-8. Genes and toxins of novel WAR- and SUP-classes are also disclosed. Certain MIS-1 and MIS-2 toxins and genes are also further characterized herein.

These families of toxins, and the genes which encode them, can be characterized in terms of, for example, the size of the toxin or gene, the DNA or amino acid sequence, pesticidal activity, and/or antibody reactivity. With regard to the genes encoding the novel toxin families of the subject invention, the current disclosure provides unique hybridization probes and PCR primers which can be used to identify and characterize DNA within each of the exemplified families.

In one embodiment of the subject invention, Bacillus isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

A further aspect of the subject invention is the use of the disclosed nucleotide sequences as probes to detect genes encoding Bacillus toxins which are active against pests.

Further aspects of the subject invention include the genes and isolates identified using the methods and nucleotide sequences disclosed herein. The genes thus identified encode toxins active against pests. Similarly, the isolates will have activity against these pests. In a preferred embodiment, these pests are lepidopteran or coleopteran pests.

In a preferred embodiment, the subject invention concerns plants cells transformed with at least one polynucleotide sequence of the subject invention such that the transformed plant cells express pesticidal toxins in tissues consumed by target pests. As described herein, the toxins useful according to the subject invention may be chimeric toxins produced by combining portions of multiple toxins. In addition, mixtures and/or combinations of toxins can be used according to the subject invention.

Transformation of plants with the genetic constructs disclosed herein can be accomplished using techniques well known to those skilled in the art and would typically involve modification of the gene to optimize expression of the toxin in plants.

Alternatively, the Bacillus isolates of the subject invention, or recombinant microbes expressing the toxins described herein, can be used to control pests. In this regard, the invention includes the treatment of substantially intact Bacillus cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

BRIEF DESCRIPTION OF THE SEQUENCES

SEQ ID NO. 1 is a nucleotide sequence encoding a toxin from *B.t.* strain Javelin 1990.

SEQ ID NO. 2 is an amino acid sequence for the Javelin 1990 toxin.

SEQ ID NO. 3 is a forward primer used according to the subject invention.

SEQ ID NO. 4 is a reverse primer used according to the subject invention.

SEQ ID NO. 5 is a nucleotide sequence of a toxin gene from *B.t.* strain PS66D3

SEQ ID NO. 6 is an amino acid sequence from the 66D3 toxin.

SEQ ID NO. 7 is a nucleotide sequence of a MIS toxin gene from *B.t.* strain PS177C8.

SEQ ID NO. 8 is an amino acid sequence from the 177C8-MIS toxin.

SEQ ID NO. 9 is a nucleotide sequence of a toxin gene from *B.t.* strain PS177I8

SEQ ID NO. 10 is an amino acid sequence from the 177I8 toxin.

SEQ ID NO. 11 is a nucleotide sequence encoding a 177C8-WAR toxin gene from *B.t.* strain PS177C8.

SEQ ID NO. 12 is an amino acid sequence of a 177C8-WAR toxin from *B.t.* strain PS177C8.

SEQ ID NOS. 13–21 are primers used according to the subject invention.

SEQ ID NO. 22 is the reverse complement of the primer of SEQ ID NO. 14.

SEQ ID NO. 23 is the reverse complement of the primer of SEQ ID NO. 15.

SEQ ID NO. 24 is the reverse complement of the primer of SEQ ID NO. 17.

SEQ ID NO. 25 is the reverse complement of the primer of SEQ ID NO. 18.

SEQ ID NO. 26 is the reverse complement of the primer of SEQ ID NO. 19.

SEQ ID NO. 27 is the reverse complement of the primer of SEQ ID NO. 20.

SEQ ID NO. 28 is the reverse complement of the primer of SEQ ID NO. 21.

SEQ ID NO. 29 is a MIS-7 forward primer.

SEQ ID NO. 30 is a MIS-7 reverse primer.

SEQ ID NO. 31 is a MIS-8 forward primer.

SEQ ID NO. 32 is a MIS-8 reverse primer.

SEQ ID NO. 33 is a nucleotide sequence of a MIS-7 toxin gene designated 157C1-A from *B.t.* strain PS157C1.

SEQ ID NO. 34 is an amino acid sequence of a MIS-7 toxin designated 157C1-A from *B.t.* strain PS157C1.

SEQ ID NO. 35 is a nucleotide sequence of a MIS-7 toxin gene from *B.t.* strain PS201Z.

SEQ ID NO. 36 is a nucleotide sequence of a MIS-8 toxin gene from *B.t.* strain PS31F2.

SEQ ID NO. 37 is a nucleotide sequence of a MIS-8 toxin gene from *B.t.* strain PS185Y2.

SEQ ID NO. 38 is a nucleotide sequence of a MIS-1 toxin gene from *B.t.* strain PS33F1.

SEQ ID NO. 39 is a MIS primer for use according to the subject invention.

SEQ ID NO. 40 is a MIS primer for use according to the subject invention.

SEQ ID NO. 41 is a WAR primer for use according to the subject invention.

SEQ ID NO. 42 is a WAR primer for use according to the subject invention.

SEQ ID NO. 43 is a partial nucleotide sequence for a MIS-7 gene from PS205C.

SEQ ID NO. 44 is a partial amino acid sequence for a MIS-7 toxin from PS205C.

SEQ ID NO. 45 is a partial nucleotide sequence for a WAR gene from PS205C.

SEQ ID NO. 46 is a partial amino acid sequence for a WAR toxin from PS205C.

SEQ ID NO. 47 is a nucleotide sequence for a MIS-8 gene from PS31F2.

SEQ ID NO. 48 is an amino acid sequence for a MIS-8 toxin from PS31F2.

SEQ ID NO. 49 is a nucleotide sequence for a WAR gene from PS31F2.

SEQ ID NO. 50 is an amino acid sequence for a WAR toxin from PS31F2.

SEQ ID NO. 51 is a SUP primer for use according to the subject invention.

SEQ ID NO. 52 is a SUP primer for use according to the subject invention.

SEQ ID NO. 53 is a nucleotide sequence for a SUP gene from KB59A4-6.

SEQ ID NO. 54 is an amino acid sequence for a SUP toxin from KB59A4-6.

DETAILED DISCLOSURE OF THE INVENTION

The subject invention concerns materials and methods for the control of non-mammalian pests. In specific embodiments, the subject invention pertains to new *Bacillus thuringiensis* isolates and toxins which have activity against lepidopterans and/or coleopterans. The subject invention further concerns novel genes which encode pesticidal toxins and novel methods for identifying and characterizing Bacillus genes which encode toxins with useful properties. The subject invention concerns not only the polynucleotide sequences which encode these toxins, but also the use of these polynucleotide sequences to produce recombinant hosts which express the toxins. The proteins of the subject invention are distinct from protein toxins which have previously been isolated from *Bacillus thuringiensis.*

*B.t.* isolates useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the *B.t.* strains are as follows:

TABLE 1

| Culture | Repository No. | Deposit Date | Patent No. |
|---|---|---|---|
| B.t. PS157C1 (MT104) | NRRL B-18240 | Jul. 17, 1987 | 5,262,159 |
| B.t. PS31F2 | NRRL B-21876 | Oct. 24, 1997 | |
| B.t. PS66D3 | NRRL B-21858 | Oct. 24, 1997 | |
| B.t. PS177C8a | NRRL B-21867 | Oct. 24, 1997 | |
| B.t. PS177I8 | NRRL B-21868 | Oct. 24, 1997 | |
| KB53A49-4 | NRRL B-21879 | Oct. 24, 1997 | |
| KB68B46-2 | NRRL B-21877 | Oct. 24, 1997 | |
| KB68B51-2 | NRRL B-21880 | Oct. 24, 1997 | |
| KB68B55-2 | NRRL B-21878 | Oct. 24, 1997 | |
| PS33F1 | NRRL B-21977 | Apr. 24, 1998 | |
| PS71G4 | NRRL B-21978 | Apr. 24, 1998 | |
| PS86D1 | NRRL B-21979 | Apr. 24, 1998 | |
| 5185V2 | NRRL B-21980 | Apr. 24, 1998 | |
| S191A21 | NRRL B-21981 | Apr. 24, 1998 | |
| P5201Z | NRRL B-21982 | Apr. 24, 1998 | |
| PS205A3 | NRRL B-21983 | Apr. 24, 1998 | |
| PS205C | NRRL B-21984 | Apr. 24, 1998 | |
| PS234E1 | NRRL B-21985 | Apr. 24, 1998 | |
| P5248N10 | NRRL B-21986 | Apr. 24, 1998 | |
| KB63B19-13 | NRRL B-21990 | Apr. 29, 1998 | |
| KB63B19-7 | NRRL B-21989 | Apr. 29, 1998 | |
| KB68B62-7 | NRRL B-21991 | Apr. 29, 1998 | |
| KB68B63-2 | NRRL B-21992 | Apr. 29, 1998 | |
| KB69A125-1 | NRRL B-21993 | Apr. 29, 1998 | |
| KB69A125-3 | NRRL B-21994 | Apr. 29, 1998 | |
| KB69A125-5 | NRRL B-21995 | Apr. 29, 1998 | |
| KB69A127-7 | NRRL B-21996 | Apr. 29, 1998 | |
| KB69A132-1 | NRRL B-21997 | Apr. 29, 1998 | |
| KB69B2-1 | NRRL B-21998 | Apr. 29, 1998 | |
| KB70B5-3 | NRRL B-21999 | Apr. 29, 1998 | |
| KB71A125-15 | NRRL B-30001 | Apr. 29, 1998 | |
| KB71A35-6 | NRRL B-30000 | Apr. 29, 1998 | |
| KB71A72-1 | NRRL B-21987 | Apr. 29, 1998 | |
| KB71A134-2 | NRRL B-21988 | Apr. 29, 1998 | |
| P5185Y2 | NRRL B-30121 | May 4, 1999 | |
| KBS9A4-6 | NRRL B-30173 | Aug. 5, 1999 | |
| MR992 | NRRL B-30124 | May 4, 1999 | |
| MR983 | NRRL B-30123 | May 4, 1999 | |
| MR993 | NRRL B-30125 | May 4, 1999 | |
| MR951 | NRRL B-30122 | May 4, 1999 | |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Many of the strains useful according to the subject invention are readily available by virtue of the issuance of patents disclosing these strains or by their deposit in public collections or by their inclusion in commercial products. For example, the *B.t.* strain used in the commercial product, Javelin, and the HD isolates are all publicly available.

Mutants of the isolates referred to herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

In one embodiment, the subject invention concerns materials and methods including nucleotide primers and probes for isolating, characterizing, and identifying Bacillus genes encoding protein toxins which are active against non-mammalian pests. The nucleotide sequences described herein can also be used to identify new pesticidal Bacillus isolates. The invention further concerns the genes, isolates, and toxins identified using the methods and materials disclosed herein.

The new toxins and polynucleotide sequences provided here are defined according to several parameters. One characteristic of the toxins described herein is pesticidal activity. In a specific embodiment, these toxins have activity against coleopteran and/or lepidopteran pests. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers. The toxins provided herein can also be identified based on their immunoreactivity with certain antibodies.

An important aspect of the subject invention is the identification and characterization of new families of Bacillus toxins, and genes which encode these toxins. These families have been designated MIS-7 and MIS-8. New WAR- and SUP-type toxin families are also disclosed herein. Toxins within these families, as well as genes encoding toxins within these families, can readily be identified as described herein by, for example, size, amino acid or DNA sequence, and antibody reactivity. Amino acid and DNA sequence characteristics include homology with exemplified sequences, ability to hybridize with DNA probes, and ability to be amplified with specific primers.

A gene and toxin (which are obtainable from PS33F1) of the MIS-1 family and a gene and toxin (which are obtainable from PS66D3) of the MIS-2 family are also further characterized herein.

A novel family of toxins identified herein is the MIS-7 family. This family includes toxins which can be obtained from *B.t.* isolates PS157C1, PS205C, and PS201Z. The subject invention further provides probes and primers for identification of the MIS-7 genes and toxins.

A further, novel family of toxins identified herein is the MIS-8 family. This family includes toxins which can be obtained from *B.t.* isolates PS31F2 and PS185Y2. The subject invention further provides probes and primers for identification of the MIS-8 genes and toxins.

In a preferred embodiment, the genes of the MIS family encode toxins having a molecular weight of about 70 to about 100 kDa and, most preferably, the toxins have a size of about 80 kDa. Typically, these toxins are soluble and can be obtained from the supernatant of Bacillus cultures as described herein. These toxins have toxicity against non-mammalian pests. In a preferred embodiment, these toxins have activity against coleopteran pests. The MIS proteins are further useful due to their ability to form pores in cells. These proteins can be used with second entities including, for example, other proteins. When used with a second entity, the MIS protein will facilitate entry of the second agent into a target cell. In a preferred embodiment, the MIS protein interacts with MIS receptors in a target cell and causes pore formation in the target cell. The second entity may be a toxin or another molecule whose entry into the cell is desired.

The subject invention further concerns a family of toxins designated WAR-type toxins. The WAR toxins typically have a size of about 30–50 kDa and, most typically, have a size of about 40 kDa. Typically, these toxins are soluble and can be obtained from the supernatant of Bacillus cultures as described herein. The WAR toxins can be identified with primers described herein as well as with antibodies.

An additional family of toxins provided according to the subject invention are the toxins designated SUP-type toxins. Typically, these toxins are soluble and can be obtained from the supernatant of Bacillus cultures as described herein. In a preferred embodiment, the SUP toxins are active against lepidopteran pests. The SUP toxins typically have a size of about 70–100 kDa and, preferably, about 80 kDa. The SUP family is exemplified herein by toxins from isolate KB59A4-6. The subject invention provides probes and primers useful for the identification of toxins and genes in the SUP family.

The subject invention also provides additional Bacillus toxins and genes, including additional MIS, WAR, and SUP toxins and genes.

Toxins in the MIS, WAR, and SUP families are all soluble and can be obtained as described herein from the supernatant of Bacillus cultures. These toxins can be used alone or in combination with other toxins to control pests. For example, toxins from the MIS families may be used in conjunction with WAR-type toxins to achieve control of pests, particularly coleopteran pests. These toxins may be used, for example, with δ-endotoxins which are obtained from Bacillus isolates.

Table 2 provides a summary of the novel families of toxins and genes of the subject invention. Certain MIS families are specifically exemplified herein by toxins which can be obtained from particular *B.t.* isolates as shown in Table 2. Genes encoding toxins in each of these families can be identified by a variety of highly specific parameters, including the ability to hybridize with the particular probes set forth in Table 2. Sequence identity in excess of about 80% with the probes set forth in Table 2 can also be used to identify the genes of the various families. Also exemplified are particular primer pairs which can be used to amplify the genes of the subject invention. A portion of a gene within the indicated families would typically be amplifiable with at least one of the enumerated primer pairs. In a preferred embodiment, the amplified portion would be of approximately the indicated fragment size. Primers shown in Table 2 consist of polynucleotide sequences which encode peptides as shown in the sequence listing attached hereto. Additional primers and probes can readily be constructed by those skilled in the art such that alternate polynucleotide sequences encoding the same amino acid sequences can be used to identify and/or characterize additional genes encoding pesticidal toxins. In a preferred embodiment, these additional toxins, and their genes, could be obtained from Bacillus isolates.

TABLE 2

| Family | Isolates | Probes (SEQ ID NO.) | Primer Pairs (SEQ ID NOS.) | Fragment size (nt) |
|---|---|---|---|---|
| MIS-1 | PS33F1 | 37 | 13 and 22 | 69 |
| | | | 13 and 23 | 506 |
| | | | 14 and 23 | 458 |
| MIS-2 | PS66D3 | 5 | 16 and 24 | 160 |
| | | | 16 and 25 | 239 |
| | | | 16 and 26 | 400 |
| | | | 16 and 27 | 509 |
| | | | 16 and 28 | 703 |
| | | | 17 and 25 | 102 |
| | | | 17 and 26 | 263 |
| | | | 17 and 27 | 372 |
| | | | 17 and 28 | 566 |
| | | | 18 and 26 | 191 |
| | | | 18 and 27 | 300 |
| | | | 18 and 28 | 494 |
| | | | 19 and 27 | 131 |
| | | | 19 and 28 | 325 |
| | | | 20 and 28 | 213 |
| MIS-7 | PS205C, PS157C1 (157C1-A), PS201Z | 33, 35 | 29 and 30 | 598 |
| MIS-8 | PS31F2, PS185Y2 | 36, 37 | 31 and 32 | 585 |
| SUP | KB59A4-6 | 1 | 51 and 52 | |

Furthermore, chimeric toxins may be used according to the subject invention. Methods have been developed for making useful chimeric toxins by combining portions of *B.t.* proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:4037–4041; Ge, A. Z., D. Rivers, R. Milne, D. H. Dean (1991) *J. Biol. Chem.* 266:17954–17958; Schnepf, H. E., K. Tomczak, J. P. Ortega, H. R. Whiteley (1990) *J. Biol. Chem.* 265:20923–20930; Honee, G., D. Convents, J. Van Rie, S. Jansens, M. Peferoen, B. Visser (1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteriol.* 172:2826–2832; Bosch, D., B. Schipper, H. van der Kliej, R. A. de Maagd, W. J. Stickema (1994) *Biotechnology* 12:915–918. A number of other methods are known in the art by which such chimeric DNAs can be made. The subject invention is meant to include chimeric proteins that utilize the novel sequences identified in the subject application.

With the teachings provided herein, one skilled in the art could readily produce and use the various toxins and polynucleotide sequences described herein.

Genes and toxins. The genes and toxins useful according to the subject invention include not only the full length sequences but also fragments of these sequences, variants, mutants, and fusion proteins which retain the characteristic pesticidal activity of the toxins specifically exemplified herein. Chimeric genes and toxins, produced by combining portions from more than one Bacillus toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins. For example, U.S. Pat. No. 5,605,793 describes methods for generating additional molecular diversity by using DNA reassembly after random fragmentation.

It is apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from Bacillus isolates and/or DNA libraries using the teachings provided herein. There are a number of methods for obtaining the pesticidal toxins of the instant invention. For example, antibodies to the pesticidal toxins disclosed and claimed herein can be used to identify and isolate toxins from a mixture of proteins. Specifically, antibodies may be raised to the portions of the toxins which are most constant and most distinct from other Bacillus toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins are within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 60%, preferably be greater than 75%, more preferably greater than 80%, more preferably greater than 90%, and can be greater than 95%. These identities are as determined using standard alignment techniques. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 3 provides a listing of examples of amino acids belonging to each class.

TABLE 3

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The δ-endotoxins of the subject invention can also be characterized in terms of the shape and location of toxin inclusions, which are described above.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

Recombinant hosts. The toxin-encoding genes of the subject invention can be introduced into a wide variety of microbial or plant hosts. Expression of the toxin gene results, directly or indirectly, in the production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be killed and treated under conditions that prolong the activity of the toxin and stabilize the cell. The treated cell, which retains the toxic activity, then can be applied to the environment of the target pest.

Where the Bacillus toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodtorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. dorus, Kluyveromyces veronae*, and *Aureobasidium pollulans*. Of particular interest are the pigmented microorganisms.

A wide variety of ways are available for introducing a Bacillus gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Synthetic genes which are functionally equivalent to the toxins of the subject invention can also be used to transform hosts. Methods for the production of synthetic genes can be found in, for example, U.S. Pat. No. 5,380,831.

Treatment of cells. As mentioned above, Bacillus or recombinant cells expressing a Bacillus toxin can be treated to prolong the toxin activity and stabilize the cell. The pesticide microcapsule that is formed comprises the Bacillus toxin within a cellular structure that has been stabilized and will protect the toxin when the microcapsule is applied to the environment of the target pest. Suitable host cells may include either prokaryotes or eukaryotes. As hosts, of particular interest will be the prokaryotes and the lower eukaryotes, such as fungi. The cell will usually be intact and be substantially in the proliferative form when treated, rather than in a spore form.

Treatment of the microbial cell, e.g., a microbe containing the Bacillus toxin gene, can be by chemical or physical means, or by a combination of chemical and/or physical means, so long as the technique does not deleteriously affect the properties of the toxin, nor diminish the cellular capability of protecting the toxin. Methods for treatment of microbial cells are disclosed in U.S. Pat. Nos. 4,695,455 and 4,695,462, which are incorporated herein by reference.

Methods and formulations for control of pests. Control of pests using the isolates, toxins, and genes of the subject invention can be accomplished by a variety of methods known to those skilled in the art. These methods include, for example, the application of Bacillus isolates to the pests (or their location), the application of recombinant microbes to the pests (or their locations), and the transformation of plants with genes which encode the pesticidal toxins of the subject invention. Transformations can be made by those skilled in the art using standard techniques. Materials necessary for these transformations are disclosed herein or are otherwise readily available to the skilled artisan.

Formulated bait granules containing an attractant and the toxins of the Bacillus isolates, or recombinant microbes comprising the genes obtainable from the Bacillus isolates disclosed herein, can be applied to the soil. Formulated product can also be applied as a seed-coating or root treatment or total plant treatment at later stages of the crop cycle. Plant and soil treatments of Bacillus cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations that contain cells will generally have from about 102 to about 104 cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Polynucleotide probes. It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA, DNA, or PNA (peptide nucleic acid). The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a toxin of interest. The probe need not have perfect complementarity to the sequence to which it hybridizes. The probes may be labelled utilizing techniques which are well known to those skilled in this art.

One approach for the use of the subject invention as probes entails first identifying by Southern blot analysis of a gene bank of the Bacillus isolate all DNA segments homologous with the disclosed nucleotide sequences. Thus, it is possible, without the aid of biological analysis, to know in advance the probable activity of many new Bacillus isolates, and of the individual gene products expressed by a given Bacillus isolate. Such a probe analysis provides a rapid method for identifying potentially commercially valuable insecticidal toxin genes within the multifarious subspecies of B.t.

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane.

The particular hybridization technique is not essential to the subject invention. As improvements are made in hybridization techniques, they can be readily applied.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or perixodases, or the various chemilurninescers such as luciferin, or fluorescent compounds like fluorescein and its derivatives. The probes may be made inherently fluorescent as described in International Application No. WO 93/16094.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170.

As used herein "moderate to high stringency" conditions for hybridization refers to conditions which achieve the same, or about the same, degree of specificity of hybridization as the conditions employed by the current applicants. Examples of moderate and high stringency conditions are provided herein. Specifically, hybridization of immobilized DNA on Southern blots with 32P-labeled gene-specific probes was performed by standard methods (Maniatis et al.). In general, hybridization and subsequent washes were carried out under moderate to high stringency conditions that allowed for detection of target sequences with homology to the exemplified toxin genes. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

Tm=81.5° C.+16.6 Log[Na+]+0.41(%G+C)−0.61 (%formamide)−600/length of duplex in base pairs.

Washes are typically carried out as follows:

(1) Twice at room temperature for 15 minutes in 1×SSPE, 0.1% SDS (low stringency wash).

(2) Once at Tm−20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

Tm (° C.)=2(number T/A base pairs)+4(number G/C base pairs) (Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant probe to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as *Taq* polymerase, which is isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan.

All of the references cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing of Bacillus Isolates Useful According to the Invention

The cellular host containing the Bacillus insecticidal gene may be grown in any convenient nutrient medium. These cells may then be harvested in accordance with conventional ways. Alternatively, the cells can be treated prior to harvesting.

The Bacillus cells of the invention can be cultured using standard art media and fermentation techniques. During the fermentation cycle, the bacteria can be harvested by first separating the Bacillus vegetative cells, spores, crystals, and lysed cellular debris from the fermentation broth by means well known in the art. Any Bacillus spores or crystal δ-endotoxins formed can be recovered employing well-known techniques and used as a conventional δ-endotoxin *B.t.* preparation. The supernatant from the fermentation process contains toxins of the present invention. The toxins are isolated and purified employing well-known techniques.

A subculture of Bacillus isolates, or mutants thereof, can be used to inoculate the following medium, known as TB broth:

| | |
|---|---|
| Tryptone | 12 g/l |
| Yeast Extract | 24 g/l |
| Glycerol | 4 g/l |
| $KH_2PO_4$ | 2.1 g/l |
| $K_2HPO_4$ | 14.7 g/l |
| pH | 7.4 |

The potassium phosphate was added to the autoclaved broth after cooling. Flasks were incubated at 30° C. on a rotary shaker at 250 rpm for 24–36 hours.

The above procedure can be readily scaled up to large fermentors by procedures well known in the art.

The Bacillus obtained in the above fermentation, can be isolated by procedures well known in the art. A frequently-used procedure is to subject the harvested fermentation broth to separation techniques, e.g., centrifugation. In a specific embodiment, Bacillus proteins useful according the present invention can be obtained from the supernatant. The culture supernatant containing the active protein(s) can be used in bioassays.

Alternatively, a subculture of Bacillus isolates, or mutants thereof, can be used to inoculate the following peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH | 7.2 |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The Bacillus spores and/or crystals, obtained in the above fermentation, can be isolated by procedures well known in the art. A frequently-used procedure is to subject the harvested fermentation broth to separation techniques, e.g., centrifugation.

EXAMPLE 2

Isolation and Preparation of Cellular DNA for PCR

DNA can be prepared from cells grown on Spizizen's agar, or other minimal or enriched agar known to those skilled in the art, for approximately 16 hours. Spizizen's casamino acid agar comprises 23.2 g/l Spizizen's minimal salts [$(NH_4)_2SO_4$, 120 g; $K_2HPO_4$, 840 g; $KH_2PO_4$, 360 g; sodium citrate, 60 g; $MgSO_4$. $7H_2O$, 12 g. Total: 1392 g]; 1.0 g/l vitamin-free casamino acids; 15.0 g/l Difco agar. In preparing the agar, the mixture was autoclaved for 30 minutes, then a sterile, 50% glucose solution can be added to a final concentration of 0.5% (1/100 vol). Once the cells are grown for about 16 hours, an approximately 1 $cm^2$ patch of cells can be scraped from the agar into 300 $\mu$l of 10 mM Tris-HCl (pH 8.0)–1 mM EDTA. Proteinase K was added to 50 $\mu$g/ml and incubated at 55° C. for 15 minutes. Other suitable proteases lacking nuclease activity can be used. The samples were then placed in a boiling water bath for 15 minutes to inactivate the proteinase and denature the DNA. This also precipitates unwanted components. The samples are then centrifuged at 14,000×g in an Eppendorf microfuge at room temperature for 5 minutes to remove cellular debris. The supernatants containing crude DNA were transferred to fresh tubes and frozen at −20° C. until used in PCR reactions.

Alternatively, total cellular DNA may be prepared from plate-grown cells using the QIAamp Tissue Kit from Qiagen (Santa Clarita, Calif.) following instructions from the manufacturer.

EXAMPLE 3

Primers Useful for Characterizing and/or Identifying Toxin Genes

The following set of PCR primers can be used to identify and/or characterize genes of the subject invention, which encode pesticidal toxins:

GGRTTAMTTGGRTAYTATTT (SEQ ID NO. 3)

ATATCKWAYATTKGCATTTA (SEQ ID NO. 4)

Redundant nucleotide codes used throughout the subject disclosure are in accordance with the IUPAC convention and include:

R=A or G

M=A or C

Y=C or T

K=G or T

W=A or T

EXAMPLE 4

Identification and Sequencing of Genes Encoding Novel Soluble Protein Toxins From Bacillus Strains PCR using primers SEQ ID NO. 3 and SEQ ID NO. 4 was performed on total cellular genomic DNA isolated from a broad range of *B.t.* strains. Those samples yielding an approximately 1 kb band were selected for characterization by DNA sequencing. Amplified DNA fragments were first cloned into the PCR DNA TA-cloning plasmid vector, pCR2.1, as described by the supplier (Invitrogen, San Diego, Calif.). Plasmids were isolated from recombinant clones and tested for the presence of an approximately 1 kbp insert by PCR using the plasmid vector primers, T3 and T7.

The following strains yielded the expected band of approximately 1000 bp, thus indicating the presence of a MIS-type toxin gene: PS66D3, PS177C8, PS177I8, PS33F1, PS157C1 (157C1-A), PS201Z, PS31F2, and PS185Y2.

Plasmids were then isolated for use as sequencing templates using QIAGEN (Santa Clarita, Calif.) miniprep kits as described by the supplier. Sequencing reactions were performed using the Dye Terminator Cycle Sequencing Ready Reaction Kit from PE Applied Biosystems. Sequencing reactions were run on a ABI PRISM 377 Automated Sequencer. Sequence data was collected, edited, and assembled using the ABI PRISM 377 Collection, Factura, and AutoAssembler software from PE ABI. DNA sequences were determined for portions of novel toxin genes from the following isolates: PS66D3, PS177C8, PS177I8, PS33F1, PS157C1 (157C1-A), PS201Z, PS31F2, and PS185Y2. These nucleotide sequences are shown in SEQ ID NOS. 5, 7, 9, 38, 33, 35, 36, and 37, respectively. Polypeptide sequences were deduced for portions of the encoded, novel soluble toxins from the following isolates: PS66D3, PS177C8, PS177I8, and PS157C1 (toxin 157C1-A). These nucleotide sequences are shown in SEQ ID NOS. 6, 8, 10, and 34, respectively.

EXAMPLE 5

Restriction Fragment Length Polymorphism (RFLP) of Toxins From *Bacillus thuringiensis* Strains Total cellular DNA was prepared from various *Bacillus thuriengensis* (*B.t.*) strains grown to an optical density of 0.5–0.8 at 600 nm visible light. DNA was extracted using the Qiagen Genomic-tip 500/G kit and Genomic DNA Buffer Set according to protocol for Gram positive bacteria (Qiagen Inc.; Valencia, Calif.).

Standard Southern hybridizations using $^{32}$P-lableled probes were used to identifiy and characterize novel toxin genes within the total genomic DNA preparations. Prepared total genomic DNA was digested with various restriction enzymes, electrophoresed on a 1% agarose gel, and immobilized on a supported nylon membrane using standard methods (Maniatis et al.).

PCR-amplified DNA fragments 1.0–1.1 kb in length were gel purified for use as probes. Approximately 25 ng of each DNA fragment was used as a template for priming nascent DNA synthesis using DNA polymerase I Klenow fragment (New England Biolabs), random hexanucleotide primers (Boehringer Mannheim) and $^{32}$PdCTP.

Each $^{32}$P-lableled fragment served as a specific probe to its corresponding genomic DNA blot. Hybridizations of immobilized DNA with randomly labeled $^{32}$P probes were performed in standard aqueous buffer consisting of 5×SSPE, 5×Denhardt's solution, 0.5% SDS, 0.1 mg/ml at 65° C. overnight. Blots were washed under moderate stringency in 0.2×SSC, 0.1% SDS at 65° C. and exposed to film. RFLP data showing specific hybridization bands containing all or part of the novel gene of interest was obtained for each strain.

TABLE 3

| (Strain)/ Gene Name | Probe Seq I.D. Number | RFLP Data (approximate band sizes) |
|---|---|---|
| (PS)66D3 | 24 | BamHI: 4.5 kbp, HindIII: >23 kbp, KpnI: 23 kbp, PstI: 15 kbp, XbaI: >23 kbp |
| (PS)177I8 | 33 | BamHI: >23 kbp, EcoRI: 10 kbp, HindIII: 2 kbp, SalI: >23 kbp, XabI: 3.5 kbp |

In separate experiments, alternative probes for MIS and WAR genes were used to detect novel toxin genes on Southern blots of genomic DNA by $^{32}$P autoradiography or by non-radioactive methods using the DIG nucleic acid labeling and detection system (Boehringer Mannheim; Indianapolis, Ind.). DNA fragments approximately 2.6 kbp (PS177C8 MIS toxin gene; SEQ ID NO. 7) and 1.3 kbp (PS177C8 WAR toxin gene; SEQ ID NO. 11) in length were PCR amplified from plasmid pMYC2450 using primers homologous to the 5' and 3' ends of each respective gene. pMYC2450 is a recombinant plasmid containing the PS177C8 MIS and WAR genes on an approximately 14 kbp ClaI fragment in pHTBlueII (an *E. coli*/*B. thuringiensis* shuttle vector comprised of pBluescript S/K [Stratagene, La Jolla, Calif.] and the replication origin from a resident *B.t.* plasmed [D. Lereclus et al. 1989; FEMS Microbiology Letters 60:211–218]). These DNA fragments were used as probes for MIS RFLP classes A through N and WAR RFLP classes A through L. RFLP data in Table 4 for class O was generated using MIS fragments approximately 1636 bp amplified with primers S1-633F (CACTCAAAAAATGAAAAGGGAAA; SEQ ID NO. 39) and S1-2269R (CCGGTTTTATTGATGCTAC; SEQ ID NO. 40). RFLP data in Table 5 for class M was generated using WAR fragments approximately 495 bp amplified with primers S2-501F (AGAACAATTTTTAGATAGGG; SEQ ID NO. 41) and S2-995R (TCCCTAAAGCATCAGAAATA; SEQ ID NO 42).

Fragments were gel purified and approximately 25 ng of each DNA fragment was randomly labeled with $^{32}$P for radioactive detection or approximately 300 ng of each DNA fragment was randomly labeled with the DIG High Prime kit for nonradioactive detection. Hybridization of immobilized DNA with randomly labeled $^{32}$P probes were performed in standard formamide conditions: 50% formamide, 5×SSPE, 5×Denhardt's solution, 2% SDS, 0.1 mg/ml sonicated sperm DNA at 42° C. overnight. Blots were washed under low stringency in 2×SSC, 0.1% SDS at 42° C. and exposed to film. RFLP data showing DNA bands containing all or part of the novel gene of interest was obtained for each strain.

RFLP data using MIS probes as discussed above were as follows:

TABLE 4

| RFLP Class | Strain Name(s) | RFLP Data (approximate band size in base pairs) |
|---|---|---|
| A | 177C8, 74H3, 66D3 | HindIII: 2,454; 1,645<br>XbaI: 14,820; 9,612; 8,138; 5,642; 1,440 |
| B | 177I8 | HindIII: 2,454<br>XbaI: 3,500 (very faint 7,000) |
| C | 66D3 | HindIII: 2,454 (faint 20,000)<br>XbaI: 3,500 (faint 7,000) |
| D | 28M, 31F2, 71G5, 71G7, 71I1, 71N1, 146F, 185Y2, 201JJ7, KB73, KB68B46-2, KB71A35-4, KB71A116-1 | HindIII: 11,738; 7,614<br>XbaI: 10,622; 6,030 |
| $D_1$ | 70B2, 71C2 | HindIII: 11,738; 8,698; 7,614<br>XbaI: 11,354; 10,622; 6,030 |
| E | KB68B51-2, KB68B55-2 | HindIII: 6,975; 2,527<br>XbaI: 10,000; 6,144 |
| F | KB53A49-4 | HindIII: 5,766<br>XbaI: 6,757 |
| G | 86D1 | HindIII: 4,920<br>XbaI: 11,961 |
| H | HD573B, 33F1, 67B3 | HindIII: 6,558; 1,978<br>XbaI: 7,815; 6,558 |
| I | 205C, 40C1 | HindIII: 6,752<br>XbaI: 4,618 |
| J | 130A3, 143A2, 157C1 | HindIII: 9,639; 3,943, 1,954; 1,210<br>XbaI: 7,005; 6,165; 4,480; 3,699 |
| K | 201Z | HindIII: 9,639; 4,339<br>XbaI: 7,232; 6,365 |
| L | 71G4 | HindIII: 7,005<br>XbaI: 9.639 |
| M | KB42A33-8, KB71A72-1, KB71A133-11 | HindIII: 3,721<br>XbaI: 3,274 |
| N | KB71A134-2 | HindIII: 7,523<br>XbaI: 10,360; 3,490 |
| O | KB69A125-3, KB69A127-7, KB69A136-2, KB7120-4 | HindIII: 6,360; 3,726; 1,874; 1,098<br>XbaI: 6,360; 5,893; 5,058; 3,726 |

RFLP data using WAR probes as discussed above were as follows:

TABLE 5

| RFLP Class | Strain Name(s) | RFLP Data (approximate band size in base pairs) |
|---|---|---|
| A | 177C8, 74H3 | HindIII: 3,659, 2,454, 606<br>XbaI: 5,457, 4,469, 1,440, 966 |
| B | 177I8, 66D3 | data unavailable |
| C | 28M, 31F2, 71G5, 71G7, 71I1, 71N1, 146F, 185Y2, 201JJ7, KB73, KB68B46-2, KB71A35-4, KB71A116-1 | HindIII: 7,614<br>XbaI: 10,982, 6,235 |
| C1 | 70B2, 71C2 | HindIII: 8,698, 7,614<br>XbaI: 11,354, 6,235 |
| D | KB68B51-2, KB68B55-2 | HindIII: 7,200<br>XbaI: 6,342 (and 11,225 for 51–2)(and 9,888 for 55–2) |
| E | KB53A49-4 | HindIII: 5,766<br>XbaI: 6,757 |
| F | HD573B, 33F1, 67B3 | HindIII: 3,348, 2,037 (and 6,558 for HD573B only)<br>XbaI: 6,953 (and 7,815, 6,185 for HD573B only) |
| G | 205C, 40C1 | HindIII: 3,158<br>XbaI: 6,558, 2,809 |
| H | 130A3, 143A2, 157C1 | HindIII: 4,339, 3,361, 1,954, 660, 349<br>XbaI: 9.043, 4,203, 3,583, 2,958, 581, 464 |
| I | 201Z | HindIII: 4,480, 3,819, 703<br>XbaI: 9,336, 3,256, 495 |
| J | 71G4 | HindIII: 7,005<br>XbaI: 9,639 |
| K | KB42A33-8, KB71A72-1, KB71A133-11 | no hybridization signal |
| L | KB71A134-2 | HindIII: 7,523<br>XbaI: 10,360 |
| M | KB69A125-3, KB69A127-7, KB69A136-2, KB71A20-4 | HindIII: 5,058; 3,726; 3,198; 2,745; 257<br>XbaI: 5,255; 4,341; 3,452; 1,490; 474 |

EXAMPLE 6

Characterization and/or Identification of WAR Toxins

In a further embodiment of the subject invention, pesticidal toxins can be characterized and/or identified by their level of reactivity with antibodies to pesticidal toxins exemplified herein. In a specific embodiment, antibodies can be raised to WAR toxins such as the toxin obtainable from PS177C8a. Other WAR toxins can then be identified and/or characterized by their reactivity with the antibodies. In a preferred embodiment, the antibodies are polyclonal antibodies. In this example, toxins with the greatest similarity to the 177C8a-WAR toxin would have the greatest reactivity with the polyclonal antibodies. WAR toxins with greater diversity react with the 177C8a polyclonal antibodies, but to a lesser extent. Toxins which immunoreact with polyclonal antibodies raised to the 177C8a WAR toxin can be obtained from, for example, the isolates designated PS177C8a, PS177I8, PS66D3, KB68B55-2, PS185Y2, KB53A49-4, KB68B51-2, PS31F2, PS74H3, PS28M, PS71G6, PS71G7, PS71I1, PS71N1, PS201JJ7, KB73, KB68B46-2, KB71A35-4, KB71A116-1, PS70B2, PS71C2, PS86D1, HD573B, PS33F1, PS67B3, PS205C, PS40C1, PS130A3, PS143A2, PS157C1, PS201Z, PS71G4, KB42A33-8, KB71A72-1, KB71A133-11, KB71A134-2, KB69A125-3, KB69A127-7, KB69A136-2, and KB71A20-4. Isolates PS31F2 and KB68B46-2 show very weak antibody reactivity, suggesting advantageous diversity.

EXAMPLE 7

Molecular Cloning and DNA Sequence Analysis of Soluble Insecticidal Protein (MIS and WAR) Genes From *Bacillus thuringiensis* Strain PS205C Total cellular DNA was prepared from *Bacillus thuringensis* strain PS205C grown to an optical density of 0.5–0.8 at 600 nm visible light in Luria Bertani (LB) broth. DNA was extracted using the Qiagen Genomic-tip 500/G kit and Genomic DNA Buffer Set according to the protocol for Gram positive bacteria (Qiagen Inc.; Valencia, Calif.). A PS205C cosmid library was constructed in the SuperCos vector (Stratragene) using inserts of PS205C total cellular DNA partially digested with Nde II. XL1-Blue cells (Stratagene) were transfected with packaged cosmids to obtain clones resistant to carbenicillin and kanamycin. 576 cosmid colonies were grown in 96-well blocks in 1 ml LB+carbenicillin (100 μg/ml)+kanamycin (50 μg/ml) at 37° C. for 18 hours and replica plated onto nylon filters for screening by hybridization.

A PCR amplicon containing approximately 1000 bp of the PS205C MIS gene was amplified from PS205 genomic DNA using primers SEQ ID NO. 3 and SEQ ID NO. 4 as described in Example 4. The DNA fragment was gel purified using QiaexII extraction (Qiagen). The probe was radiolabeled with $^{32}$P-dCTP using the Prime-It II kit (Stratgene) and used in aqueous hybridization solution (6×SSPE, 5×Denhardt's solution, 0.1% SDS, 0.1 mg/ml denatured DNA) with the colony lift filters at 65° C. for 16 hours. The colony lift filters were briefly washed 1× in 2×SSC/0. 1% SDS at room temperature followed by two additional washes for 10 minutes in 0.5×SSC/0.1% SDS. The filters were then exposed to X-ray film for 5.5 hours. One cosmid clone that hybridized strongly to the probe was selected for further analysis. This cosmid clone was confirmed to contain the MIS gene by PCR amplification with primers SEQ ID NO. 3 and SEQ ID NO. 4. This cosmid clone was designated as pMYC3105; recombinant *E. coli* XL-1Blue MR cells containing pMYC3105 are designated MR992.

A subculture of MR992 was deposited in the permanent collection of the Patent Culture Collection (NRRL), Regional Research Center, 1815 North University Street, Peoria, Ill. 61604 USA on May 4, 1999. The accession number is NRRL B-30124. A truncated plasmid clone for PS205C was also deposited on May 4, 1999. The accession number is NRRL B-30122.

To sequence the PS205C MIS and WAR genes, random transposon insertions into pMYC3105 were generated using the GPS-1 Genome Priming System and protocols (New England Biolabs). The GPS2 trasposition vector encoding chloramphenicol resistance was chosen for selection of cosmids containing insertions. pMYC3105 cosmids that acquired transposons were identified by transformation and selection of *E. coli* XL1-Blue MR on media containing ampicillin, kanamycin and chloramphenicol. Cosmid templates were prepared from individual colonies for use as sequencing templates using the Multiscreen 96-well plasmid prep (Millipore). The MIS and WAR toxin genes encoded by pMYC3105 were sequenced with GPS2 primers using the ABI377 automated sequencing system and associated software. The MIS and WAR genes were found to be located next to one another in an apparent transcriptional operon. The nucleotide and deduced polypeptide sequences are designated as new SEQ ID NOS. 43–46.

EXAMPLE 8

Molecular Cloning and DNA Sequence Analysis of Soluble Insecticidal Protein (MIS and WAR) Genes From *Bacillus Thuringensis Strain PS*31F2 a. Preparation and Cloning of Genomic DNA

Total cellular DNA was prepared from the *Bacillus thuringensis* strain PS31F2 grown to an optical density of 0.5–0.8 at 600 nm visible light in Luria Bertani (LB) broth. DNA was extracted using the Qiagen Genomic-tip 500/G kit or Genomic-Tip 20/G and Genomic DNA Buffer Set (Qiagen Inc.; Valencia, Calif.) according to the protocol for Gram positive bacteria.

Lambda libraries containing total genomic DNA from *Bacillus thuringensis* strain PS31F2 were prepared from DNA partially digested with NdeII. Partial NdeII restriction digests were electrophoresed on a 0.7% agarose gel and the region of the gel containing DNA fragments within the size range of 9–20 kbp was excised from the gel. DNA was electroeluted from the gel fragment in 0.1×TAE buffer at approximately 30 V for one hour and purified using Elutip-d columns (Schleicher and Schuell; Keene, N.H.).

Purified, fractionated DNA was ligated into BamHI-digested Lambda-GEM-11 arms (Promega Corp., Madison, Wis.). Ligated DNA was then packaged into lambda phage using Gigapack III Gold packaging extract (Stratagene Corp., La Jolla, Calif.). *E. coli* strain KW251 was infected with recombinant phage and plated onto LB plates in LB top agarose. Plaques were lifted onto nitrocellulose filters and prepared for hybridization using standard methods (Maniatis, et al.). DNA fragments approximately 1.1 kb (PS177C8 MIS) or 700 bp (PS177C8 WAR) in length were PCR amplified from plasmid pMYC2450 and used as the probes. Fragments were gel purified and approximately 25 ng of each DNA fragment was randomly labeled with $^{32}$P-dCTP. Hybridization of immobilized DNA with randomly $^{32}$P-labeled PS177C8 probes was performed in standard formamide conditions: 50% formamide, 5×SSPE, 5×Denhardt's solution, 2% SDS, 0.1 mg/ml at 42° C. overnight. Blots were washed under low stringency in 2×SSC, 0.1% SDS at 42° C. and exposed to film. Hybridizing plaques were isolated from the plates and suspended in SM buffer. Phage DNA was prepared using LambdaSorb phage adsorbent (Promega, Madison, Wis.). PCR using the oligonucleotide primers SEQ ID NO. 3 and SEQ ID NO. 4 was performed using phage DNA templates to verify the presence of the target gene. The PCR reactions yielded the expected 1 kb band in both DNA samples confirming that those phage clones contain the gene of interest. For subcloning, phage DNA was digested with various enzymes, fractionated on a 1% agarose gel and blotted for Southern analysis. Southern analysis was performed as decribed above. A HindIII fragment approximately 8 kb in size was identified that contained the PS31F2 toxin genes. This fragment was gel purified and cloned into the HindIII site of pBluescriptII (SK+); this plasmid clone is designated pMYC2610. The recombinant *E. coli* XL10Gold [pMYC2610] strain was designated MR983.

A subculture of MR983 was deposited in the permanent collection of the Patent Culture Collection (NRRL), Regional Research Center, 1815 North University Street, Peoria, Ill. 61604 USA on May 4, 1999. The accession number is NRRL B-30123.

b. DNA Sequencing

The pMYC2610 HindIII fragment containing the PS31F2 toxin genes was isolated by restriction digestion, fractionation on a 0.7% agarose gel and purification from the gel matrix using the QiaexII kit (Qiagen Inc.; Valencia, Calif.). Gel purified insert DNA was then digested separately with restriction enzymes AluI, MseI, or RsaI and fractionated on a 1% agarose gel. DNA fragments between 0.5 and 1.5 kb were excised from the gel and purified using the QiaexII kit. Recovered fragments were ligated into EcoRV digested pBluescriptII and transformed into *E. coli* XL10 Gold cells. Plasmid DNA was prepared from randomly chosen transformants, digested with NotI and ApaI to verify insert size and used as sequencing templates with primers homologous to plasmid vector sequences. Primer walking was used to complete the sequence. Sequencing reactions were performed using dRhodamine or BigDye Sequencing kit (ABI Prism/Perkin Elmer Applied Biosystems) and run on ABI 373 or 377 automated sequencers. Data was analyzed using Factura, Autoassembler (ABI Prism) and Gentics Computer Group (Madison, Wis.) programs. The MIS and WAR genes were found to be located next to one another in an apparent transcriptional operon. The WAR gene is 5' to the MIS gene, and the two genes are separated by 4 nucleotide bases.

The nucleotide sequences and deduced peptide sequences for the novel MIS and WAR genes from PS31F2 are reported as new SEQ ID NOS. 47–50.

c. Subcloning and Transformation of *B. thuringiensis*

The PS31F2 toxin genes were subcloned on the 8 kbp HinDIII fragment from pMYC2610 into the *E. coli/B.t.* shuttle vector, pHT370 (O. Arantes and D. Lereclus. 1991. Gene 108: 115–119), for expression from the native *Bacillus* promoter. The resulting plasmid construct was designated pMYC2615. pMYC2415 plasmid DNA was prepared from recombinant *E.coli* XL10Gold for transformation into the acrystallierous (Cry-) *B.t.* host, CryB (A. Aronson, Purdue University, West Lafayette, Ind.), by electroporation. The recombinant CryB [pMYC2615] strain was designated MR558.

EXAMPLE 9

Molecular Cloning and DNA Sequence Analysis of a Novel SUP Toxin Gene From *Bacillus Thuringiensis* strain KB59A4-6

Total cellular DNA was prepared from the *Bacillus thuringensis* strain KB59A4-6 grown to an optical density of 0.5–0.8 at 600 nm visible light in Luria Bertani (LB) broth. DNA was extracted using the Qiagen Genomic-tip 500/G kit and Genomic DNA Buffer Set according to the protocol for Gram positive bacteria (Qiagen Inc.; Valencia, Calif.). DNA was digested with HinDIII and run on 0.7% agarose gels for Southern blot analysis by standard methods (Maniatis et al.). A PCR amplicon containing the SUP-like gene (SEQ ID NO. 1) from Javelin-90 genomic DNA was obtained by using the oligos "3A-atg (GCTCTAGAAGGAGGTAACTTATGAACAAGAATAATACTAAATTAAGC) (SEQ ID NO. 51) and "3A-taa" (GGGGTACCTTACTTAATAGAGACATCG) (SEQ ID NO. 52). This DNA fragment was gel purified and labeled with radioactive $^{32}$P-dCTP using Prime-It II Random Primer Labeling Kit (Stratagene) for use as a probe. Hybridization of Southern blot filters was carried out in a solution of 6×SSPE, 5×Denhardt's solution, 0.1% SDS, 0.1 mg/ml denatured DNA at 42° C. overnight in a shaking water bath. The filters were subsequently washed in 1×SSPE and 0.1% SDS once at 25° C. followed by two additional washes at 37° C. Hybridized filters were then exposed to X-ray film at −80° C. An approximately 1 kbp HinDIII fragment of KB59A4-6 genomic DNA was identified that hybridized to the Javelin 90 SUP probe.

A lambda library of KB59A4-6 genomic DNA was constructed as follows. DNA was partially digested with Sau3A and size-fractionated on agarose gels. The region of the gel containing fragments between 9.0 and 23 kbp was excised and DNA was isolated by electroelution in 0.1×TAE buffer followed by purification over Elutip-d columns (Schleicher and Schuell, Keene, N.H.). Size-fractionated DNA inserts were ligated into BamHI-digested Lambda-Gem 11 (Promega) and recombinant phage were packaged using GigapackIII XL Packing Extract (Stratagene). Phage were plated on *E. coli* VCS257 cells for screening by hybridization. Plaques were transferred to nylon filters and dried under vacuum at 80° C. Hybridization was then performed with the Javelin 90 Sup gene probe as described above. One plaque that gave a positive signal was selected using a Pasteur pipette to obtain a plug. The plug was soaked over-night at room temperature in 1 mL SM buffer+10 uL $CHCl_3$. Large-scale phage DNA preparations (Maniatis et al.) were obtained from liquid lysates of *E. coli* KW251 infected with this phage.

The KB59A4-6 toxin gene was subcloned into the *E. coli/B. thuringiensis* shuttle vector, pHT370 (O. Arantes and D. Lereclus. 1991. Gene 108: 115–119), on an approximately 5.5 kbp SacI/XbaI fragment identified by Southern hybridization. This plasmid subclone was designated pMYC2473. Recombinant *E. coli* XL10-Gold cells (Stratagene) containing this construct are designated MR993. The insecticidal toxin gene was sequenced by primer walking using pMYC2473 plasmid and PCR amplicons as DNA templates. Sequencing reactions were performed using the Dye Terminator Cycle Sequencing Ready Reaction Kit from PE Applied Biosystems and run on a ABI PRISM 377 Automated Sequencer. Sequence data was analyzed using the PE ABI PRISM 377 Collection, Factura, and AutoAssembler software. The DNA sequence and deduced peptide sequence of the KB59A4-6 toxin are reported as new SEQ ID NOS. 53 and 54, respectively.

A subculture of MR993 was deposited in the permanent collection of the Patent Culture Collection (NRRL), Regional Research Center, 1815 North University Street, Peoria, Ill. 61604 USA on May 4, 1999. The accession number is NRRL B-30125.

EXAMPLE 10

Bioassays for Activity Against Lepidopterans and Coleopterans

Biological activity of the toxins and isolates of the subject invention can be confirmed using standard bioassay procedures. One such assay is the budworm-bollworm (*Heliothis virescens* [Fabricius] and *Helicoverpa zea* [Boddie]) assay. Lepidoptera bioassays were conducted with either surface application to artificial insect diet or diet incorporation of samples. All Lepidopteran insects were tested from the neonate stage to the second instar. All assays were conducted with either toasted soy flour artificial diet or black cutworm artificial diet (BioServ, Frenchtown, N.J.).

Diet incorporation can be conducted by mixing the samples with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no *B.t.* serves as the control. First instar larvae (USDA-ARS, Stoneville, Miss.) are placed onto the diet mixture. Wells are then sealed with Mylar sheeting (ClearLam Packaging, Ill.) using a tacking iron, and several pinholes are made in each well to provide gas exchange. Larvae were held at 25° C. for 6 days in a 14:10 (light:dark) holding room. Mortality and stunting are recorded after six days.

Bioassay by the top load method utilizes the same sample and diet preparations as listed above. The samples are applied to the surface of the insect diet. In a specific embodiment, surface area ranged from 0.3 to approximately 0.8 $cm^2$ depending on the tray size, 96 well tissue culture plates were used in addition to the format listed above. Following application, samples are allowed to air dry before insect infestation. A water blank containing no *B.t.* can serve as the control. Eggs are applied to each treated well and were then sealed with Mylar sheeting (ClearLam Packaging, Ill.) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of sample onto an agar-based artificial diet at a rate of 160 ml/$cm^2$. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays are held in darkness at 25° C., and mortality scored after four days.

Analogous bioassays can be performed by those skilled in the art to assess activity against other pests, such as the black cutworm (*Agrotis ipsilon*).

Results are shown in Table 6.

TABLE 6

Genetics and function of concentrated B.t. supernatants screened for lepidopteran and coleopteran activity

| Strain | Approx. 339 bp PCR fragment | Total Protein ($\mu g/cm^2$) | ca. 80–100 kDa protein ($\mu g/cm^2$) | *H. virescens* % mortality | *H. virescens* Stunting | *H. zen* % mortality | *H. zen* Stunting | Diabrotica % mortality |
|---|---|---|---|---|---|---|---|---|
| PS157C1 (#1) | — | 24 | 2 | 43 | yes | 13 | yes | — |
| PS157C1 (#2) | — | 93 | 8 | — | — | - | — | 40 |
| PS157C1 (#3) | — | 35 | 3 | - | — | — | — | 18 |
| Javelin 1990 | ++ | 43.2 | 3.6 | 100 | yes | 96 | yes | NT |
| water | | | | 0–8 | — | 0–4 | - | 12 |

EXAMPLE 11

Results of Western Corn Rootworm Bioassays and Further Characterization of the Toxins Concentrated liquid supernatant solutions, obtained according to the subject invention, were tested for activity against Western corn rootworm (WCRW). Supernatants from the following isolates were found to cause mortality against WCRW: PS31F2, PS66D3, PS177I8, KB53A49-4, KB68B46-2, KB68B51-2, KB68B55-2, and PS177C8.

Supernatants from the following isolates were also found to cause mortality against WCRW: PS205A3, PS185V2, PS234E1, PS71G4, PS248N10, PS191A21, KB63B19-13, KB63B19-7, KB68B62-7, KB68B63-2, KB69A125-1, KB69A125-3, KB69A125-5, KB69A127-7, KB69A132-1, KB69B2-1, KB70B5-3, KB71A125-15, and KB71A35-6; it was confirmed that this activity was heat labile. Furthermore, it was determined that the supernatants of the following isolates did not react (yielded negative test results) with the WAR antibody (see Example 12), and did not react with the MIS (SEQ ID NO. 31) and WAR (SEQ ID NO. 51) probes: PS205A3, PS185V2, PS234E1, PS71G4, PS248N10, PS191A21, KB63B19-13, KB63B19-7, KB68B62-7, KB68B63-2, KB69A125-1, KB69A125-5, KB69A132-1, KB69B2-1, KB70B5-3, KB71A125-15, and KB71A35-6; the supernatants of isolates KB69A125-3 and KB69A127-7 yielded positive test results.

EXAMPLE 12

Culturing of 31F2 Clones and Bioassay of 31F2 Toxins on Western Corn Rootworm (wCRW)

*E. coli* MR983 and the negative control strain MR948 (*E. coli* XL1-Blue [pSupercos]; vector control) were grown in 250 ml bottom baffled flasks containing 50 ml of DIFCO Terrific Broth medium. Cultures were incubated in New Brunswick shaker agitating at 250 RPM, 30° C. for ~23 hours. After 23 hours of incubation samples were aseptically taken to examine the cultures under the microscope to check for presence of contaminants. 30 ml of culture were dispensed into a 50 ml centrifuge tube and centrifuged in a Sorvall centrifuge at 15,000 rpm for 20 minutes. The 1× supernatant was saved and submitted for bioassay against wCRW. The pellet was resuspended 5× with 10 mM TRIS buffer, and was sonicated prior to submission for bioassay against wCRW.

*B.t.* strain MR558 and the negative control MR539 (*B.t.* cry B[pHT Blue II]; vector control) were grown in the same manner except for the omission of glycerol from the Terrific Broth medium. *B.t.* cell pellets were resuspended in water rather than buffer prior to sonication.

Assays for the *E. coli* clone MR983 and *B. thuringiensis* clone MR558 containing the 31F2 toxin genes were conducted using the same experimental design as in Example 10 for western corn rootworm with the following exceptions: Supernatant samples were top-loaded onto diet at a dose of ~160 ul/$cm^2$. *B.t.* cellular pellet samples at a 5× concentration were top-loaded onto the diet at a dose of~150 ul/ $cm^2$ for both clones, and at ~75, and at doses of ~35 ul/ cm2 for the MR558 *B. thuringiensis* clone (quantity of active toxin unknown for either clone). Approximately 6–8 larvae were transferred onto the diet immediately after the sample had evaporated. The bioassay plate was sealed with mylar sheeting using a tacking iron and pinholes were made above each well to provide gas exchange. Both the MR983 and MR558 clones demonstrated degrees of bioactivity (greater mortality) against western corn rootworm as compared to the toxin-negative clones MR948 and MR539.

Table 7 presents the results showing the bioactivity of cloned PS31F2 toxins against western corn rootworm.

TABLE 7

| Strain | Toxin genes | Rate => | Percent Mortality of wCRW Supernatant 160 ul/cm$^2$ | Pellet 5X 150 ul/cm$^2$ | Pellet 5X 75 ul/cm$^2$ | Pellet 5X 35 ul/cm$^2$ |
|---|---|---|---|---|---|---|
| MR983 | 31F2 | | 7% (4/56) | 19% (5/27) | — | — |
| MR948 | none | | 4% (1/24) | 26% (6/23) | — | — |
| MR983 | 31F2 | | 3%(5/147) | — | 20% (49/245) | — |
| MR948 | none | | 27%(19/70) | — | 51% (79/154) | — |
| MR983 | 31F2 | | 13%(32/243) | — | 33% (85/259) | — |
| MR948 | none | | 9%(14/155) | — | 20% (55/273) | — |
| MR558 | 31F2 | | 35%(41/118) | 88% (43/49) | 9%(9/100) | 13%(13/97) |
| MR539 | none | | 10%(14/134) | 14% (3/21) | 15% (17/11) | 17%(19/111) |
| MR558 | 31F2 | | 3%(1/29) | 35%(17/48) | 29%(15/52) | 13%(7/55) |
| MR539 | none | | 19%(5/27) | 20%(9/46) | 31%(18/57) | 18%(9/49) |
| MR558 | 31F2 | | 13%(9/69) | 38%(19/50) | 18%(15/85) | 15%(10/65) |
| MR539 | none | | 29%(16/55) | 24%(14/58) | 14%(13/91) | 28%(18/64) |
| MR558 | 31F2 | | 7%(5/74) | 14% (9/66) | 17%(14/83) | 11%(6/57) |
| MR539 | none | | 11%(9/79) | 32% (19/59) | 9%(7/78) | 15%(10/67) |

EXAMPLE 13

Target Pests

Toxins of the subject invention can be used, alone or in combination with other toxins, to control one or more non-mammalian pests. These pests may be, for example, those listed in Table 8. Activity can readily be confirmed using the bioassays provided herein, adaptations of these bioassays, and/or other bioassays well known to those skilled in the art.

TABLE 8

| Target pest species ORDER/Common Name | Latin Name |
|---|---|
| LEPIDOPTERA | |
| European Corn Borer | *Ostrinia nubilalis* |
| European Corn Borer resistant to Cry1A-class of toxins | *Ostrinia nubilalis* |
| Black Cutworm | *Agrotis ipsilon* |
| Fall Armyworm | *Spodoptera frugiperda* |
| Southwestern Corn Borer | *Diatraea grandioseila* |
| Corn Earworm/Bollworm | *Helicoverpa zea* |
| Tobacco Budworm | *Heliothis virescens* |
| Tobacco Budworm resistant to Cry1A-class of toxins | *Heliothis virescens* |
| Sunflower Head Moth | *Homeosoma ellectellum* |
| Banded Sunflower Moth | *Cochylis hospes* |
| Argentine Looper | *Rachiplusia nu* |
| Spilosoma | *Spilosoma virginica* |
| Bertha Armyworm | *Mamestra configurata* |
| Diamondback Moth | *Plutella xylostells* |
| Diamondback Moth resistant to Cry1A-class of toxins | *Plutella xylostells* |

TABLE 8-continued

| Target pest species ORDER/Common Name | Latin Name |
|---|---|
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| DIPTERA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | *Heterodera glycines* |

EXAMPLE 14

Insertion of Toxin Genes Into Plants

One aspect of the subject invention is the transformation of plants with genes encoding the insecticidal toxin of the present invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic Bacillus genes for use in plants are known in the art.

It should be understood that the examples and embodiments described herein are for illustrative purposes only and that various modifications or changes in light thereof will be suggested to persons skilled in the art and are to be included within the spirit and purview of this application and of the appended claims.

What is claimed is:

1. An isolated polynucleotide that encodes a pesticidally active protein, wherein said protein has at least 95% identity with the amino acid sequence of SEQ ID NO:54.

2. The polynucleotide according to claim 1, wherein said protein comprises the amino acid sequence of SEQ ID NO:54.

3. The polynucleotide according to claim 1, wherein said polynucleotide comprises the nucleotide sequence of SEQ ID NO:53.

4. A host cell comprising an isolated polynucleotide that encodes a pesticidally active protein, wherein said protein has at least 95% identity with the amino acid sequence of SEQ ID NO:54, and wherein said cell is selected from the group consisting of a plant cell and a microbial cell.

5. The cell according to claim 4, wherein said protein comprises the sequence of SEQ ID NO:54.

6. The cell according to claim 4, wherein said polynucleotide comprises the nucleotide sequence of SEQ ID NO:53.

7. The cell according to claim 4, wherein said cell is a plant cell.

8. The cell according to claim 4, wherein said cell is a microbial cell.

9. The microbial cell according to claim 7, wherein said microbial cell is a bacterial cell.

10. A transgenic plant comprising an isolated polynucleotide that encodes a pesticidally active protein, wherein said protein has at least 95% identity with the amino acid sequence of SEQ ID NO:54.

11. A The plant according to claim 10, wherein said protein comprises the sequence of SEQ ID NO:54.

12. The plant according to claim 10, wherein said polynucleotide comprises the nucleotide sequence of SEQ ID NO:53.

* * * * *

UNITED STATES PATENT AND TRADEMARK OFFICE

CERTIFICATE OF CORRECTION

PATENT NO. : 6,603,063 B1
APPLICATION NO. : 09/307106
DATED : August 5, 2003
INVENTOR(S) : Jerald S. Feitelson et al.

It is certified that error appears in the above-identified patent and that said Letters Patent is hereby corrected as shown below:

Column 2

Line 12, "subsp.kurstaki" should read --subsp. kurstaki--

Column 6

Line 41, "5185V2" should read --PS185V2--

Column 6

Line 42, "S191A21" should read --PS191A21--

Column 6 (Table 1)

Line 43, "P5201Z" should read --PS201Z--

Column 6 (Table 1)
Line 46, "P5248N10" should read --PS248N10--

Column6 (Table 1)
Line 58, "P5185Y2" should read --PS185Y2--

Column 6 (Table 1)
Line 59, "KBS9A4-6" should read --KB59A4-6--

Column 6 (Table)
Line 59, "NRRL B-30173" should read --NRRL B--

Column 6 (Table 1)
Line 59, "Aug. 5, 1999" should read --No Info--

Column 12
Line 52, "S. dorus" should read --S. odorus--

Column 13
Line 59, "102 to about 104" should read --$10^2$ to about $10^4$--

UNITED STATES PATENT AND TRADEMARK OFFICE
CERTIFICATE OF CORRECTION

PATENT NO. : 6,603,063 B1
APPLICATION NO. : 09/307106
DATED : August 5, 2003
INVENTOR(S) : Jerald S. Feitelson et al.

It is certified that error appears in the above-identified patent and that said Letters Patent is hereby corrected as shown below:

Column 29(Table 8)
Line 56, "grandioseila" should read --grandiosella--

Column 98
Line 47; Claim 9, "According to claim 7" should read --According to claim 8--

Signed and Sealed this

Twenty-fifth Day of July, 2006

JON W. DUDAS
*Director of the United States Patent and Trademark Office*